United States Patent
Hume et al.

(10) Patent No.: US 10,251,365 B2
(45) Date of Patent: Apr. 9, 2019

(54) FUNGAL ENDOPHYTES

(71) Applicants: GRASSLANZ TECHNOLOGY LIMITED, Hamilton (NZ); THE GRAINS RESEARCH AND DEVELOPMENT CORPORATION, Barton (AU)

(72) Inventors: David Edward Hume, Palmerston North (NZ); Richard David Johnson, Palmerston North (NZ); Wayne Roydon Simpson, Palmerston North (NZ); Stuart Douglas Card, Palmerston North (NZ)

(73) Assignees: THE GRAINS RESEARCH AND DEVELOPMENT CORPORATION, Barton (AU); GRASSLANZ TECHNOLOGY LIMITED, Hamilton (NZ)

( * ) Notice: Subject to any disclaimer, the term of this patent is extended or adjusted under 35 U.S.C. 154(b) by 611 days.

(21) Appl. No.: 14/772,169

(22) PCT Filed: Mar. 6, 2014

(86) PCT No.: PCT/IB2014/059479
§ 371 (c)(1),
(2) Date: Sep. 2, 2015

(87) PCT Pub. No.: WO2014/136070
PCT Pub. Date: Sep. 12, 2014

(65) Prior Publication Data
US 2016/0262335 A1    Sep. 15, 2016

Related U.S. Application Data

(60) Provisional application No. 61/773,722, filed on Mar. 6, 2013.

(51) Int. Cl.
*A01H 17/00* (2006.01)
*A01N 63/04* (2006.01)
*C12N 1/14* (2006.01)
*C12R 1/645* (2006.01)

(52) U.S. Cl.
CPC .......... *A01H 17/00* (2013.01); *A01N 63/04* (2013.01); *C12N 1/14* (2013.01); *C12R 1/645* (2013.01)

(58) Field of Classification Search
CPC .................................................. A01H 17/00
See application file for complete search history.

(56) References Cited

U.S. PATENT DOCUMENTS

2010/0024076 A1   1/2010   Craven
2012/0144533 A1   6/2012   Craven

FOREIGN PATENT DOCUMENTS

WO     WO 02/13616 A2       2/2002
WO     WO 2004/082384 A2    9/2004
WO     WO 2008/100892 A2 *  8/2008

OTHER PUBLICATIONS

AB Lloyd: "The Endophytic Fungus of Perennial Ryegrass", New Zealand Journal of Agricultural Research, Dec. 2, 1959, pp. 1187-1194, XP055293765.
Stuart D. Card et al: "Mutualistic fungal endophytes in the Triticeae—survey and description", FEMS Microbiology Ecology., vol. 88, No. 1, Jan. 21, 2014, pp. 94-106, XP055293911.
Extended European Search Report of European Application No. EP 14760058.9, dated Dec. 5, 2016.
Linda Johnson: "The Exploitation of Epichloe Endophytes for Agricultural Advantage", COST-Action "Endophytes in Biotechnology and Agriculture": Working Group 1-4 Meeting: Endophytes: From discovery to application, Trento/S. Michele, Italy Nov. 12-14, 2012, pp. 1-41, XP055293909; Retrieved from the Internet on Aug. 5, 2016: URL:http://endophytes.eu/trento2012/Trento_2012_Johnson Linda.
Johnson, L.J. et al., "The exploitation of epichloae endophytes for agricultural benefit," *Fungal Diversity*, 2013, vol. 60, pp. 171-188. Published online Jun. 1, 2013.
International Search Report and Written Opinion in corresponding PCT Application No. PCT/IB2014/059479, dated May 7, 2014.
Simpson WR, Mace WJ, Novel associations between epichloae endophytes and grasses: Possibilities and outcomes. In "Epichloae, Endophytes of Cool Season Grasses: Implications, Utilization and Biology." (Eds. CA Young, GE Aiken, RL McCulley, JR Strickland, CL Schardl), 2012, pp. 35-39. (The Samuel Roberts Noble Foundation: Ardmore, Oklahoma).

* cited by examiner

*Primary Examiner* — David H Kruse
(74) *Attorney, Agent, or Firm* — Leason Ellis LLP

(57) ABSTRACT

The present invention relates to at least one epichloae fungal endophyte strain combined with at least one species of *Secale* spp., which confers at least some level of pest protection on the *Secale* spp. plant. In particular, the invention relates to an isolated strain of epichloae fungal endophyte selected from the group consisting of AR3039 (NRRL# 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073 (NRRL# 50721), AR3074 (NRRL# 50722), AR3076 (NRRL# 50723), and AR3078 (NRRL# 50724), and combinations thereof; a *Secale* spp. plant infected with a fungal endophyte wherein *Secale* spp. is not a natural host of the endophyte; a method of making a stable host plant/epichloae fungal endophyte combination; a method of conferring at least some level of pest protection on a host *Secale* spp. plant; and a *Secale* spp. seed infected with an epichloae fungal endophyte.

18 Claims, 5 Drawing Sheets
Specification includes a Sequence Listing.

FUNGAL ENDOPHYTES

CROSS-REFERENCE TO RELATED PATENT APPLICATIONS

This application is a U.S. National Phase Application under 35 U.S.C. § 371 of International Patent Application No. PCT/IB2014/059479, filed Mar. 6, 2014, and claims the benefit of priority under 35 U.S.C. Section 119(e) of U.S. application Ser. No. 61/773,722, filed Mar. 6, 2013, all of which are incorporated by reference in their entireties. The International Application was published on Sep. 12, 2014 as International Publication No. WO 2014/36070 A1.

TECHNICAL FIELD

The present invention generally relates to an epichloae endophyte that forms a stable symbiotic association with ryecorn (*Secale cereale*).

BACKGROUND OF THE INVENTION

*Secale cereale*, commonly known as Rye, is grown worldwide, typically for the production of grain. The grain is used primarily for making flour, bread and for direct consumption, particularly in those countries having a history of rye-bread consumption. The vegetative portions of *S. cereale* may be used as straw, or converted to silage, for use as animal fodder, including for in situ grazing.

As noted above, rye is mainly grown for grain. Therefore, effective pest protection during cultivation is required to ensure that a good quantity of acceptable quality grain is produced. Rye is typically considered an autumnal crop with seeds generally sown in the fall. Crop rotation with other cereals or field crops can be used to reduce the build-up of pests and/or fungal diseases present in soil or that develop in crop debris.

Principal pests of rye include, but are not limited to, aphids; thrips; wireworms and white grubs; leatherjackets (*Tipula* spp.); wheat bulb fly (*Delia coarctata*); leaf miners (*Agromyza* spp.); frit fly (*Oscinella frit*); ground beetle (*Zabrus tenebrioides*); saddle gall midge (*Haplodiplosis marginata*); cereal leaf beetles (*Oulema melanopus, O. gallaeciana*); nematodes; and slugs.

Known methods of pest control for rye include some or all of the following practices: the use of pest resistant cultivars, optimizing time of planting and planting with healthy seeds, effective crop rotation, destruction, and/or burial or removal of crop debris (stubble). Additional methods of pest control that may be required include the use of various pesticides on plants and/or seeds. At times, simultaneous application of two or more active substances may be required for the control of pests.

However, the use of many pesticides can be problematic due to the known problems associated with the chemicals frequently used for such purposes. Many pesticides are toxic and can be dangerous to human and animal consumers of treated agricultural crops (Casida and Quistad, 1998). In particular, the accumulation, in humans and animals of toxic pesticides can lead to serious health issues for individuals, particularly during early development. For example, pesticide exposure has been linked to respiratory disorders, developmental cancers and shown to have lasting effects on the development of mental abilities Zejda et al. (1993).

The use of pesticides may be difficult to control in variable environmental conditions leading to unwanted dispersal of toxic compounds, for example by drift of sprays or by soil leaching. In addition, the pests may develop pesticide resistance for a number of reasons, including improper practice and handling, which can pose a real threat to crop (grain) yields. Accordingly there is a need for pest control measures that do not use applied pesticides.

It is an object of the present invention to provide at least one epichloae fungal endophyte strain which when combined with at least one species of *Secale* spp. confers at least some level of pest protection on the *Secale* spp. plant, and/or to provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In a first aspect, the present invention relates to an isolated strain of epichloae fungal endophyte selected from the group consisting of AR3039 (NRRL# 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073 (NRRL# 50721), AR3074 (NRRL# 50722), AR3076 (NRRL# 50723), and AR3078 (NRRL# 50724), and combinations thereof. Preferably the invention relates to strains AR3039, AR3046, AR3050, AR3067, AR3068, AR3074 and AR3078, preferably AR3046, AR3050 or AR3068.

In one embodiment, the isolated strain is biologically pure.

In a second aspect the invention relates to a *Secale* spp. plant infected with a fungal endophyte wherein *Secale* spp. is not a natural host of the endophyte, and wherein the plant and endophyte form a stable symbiotic association that allows the plant to progress through a normal life cycle.

In one embodiment the endophyte is transmitted from a first generation of *Secale* spp. to a second generation of *Secale* spp. by vertical transmission. Preferably vertical transmission from a first generation of host plant to a second generation of host plant is by seeds.

In one embodiment the endophyte is an endophyte isolated from *Elymus* spp. Preferably the endophyte is isolated from *Elymus mutabilis*. Preferably the endophyte is an epichloae endophyte. Preferably the epichloae endophyte is an epichloae endophyte strain selected from the group consisting of AR3039 (NRRL # 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073 (NRRL# 50721), AR3074 (NRRL# 50722), AR3076 (NRRL# 50723), and AR3078 (NRRL# 50724), or combinations thereof. Preferably the invention relates to endophyte strains AR3039, AR3046, AR3050, AR3067, AR3068, AR3074 and AR3078, preferably AR3046, AR3050 or AR3068.

In one embodiment the *Secale* spp. infected with the fungal endophyte shows no external symptoms of endophyte infection.

In one embodiment the *Secale* spp. infected with the fungal endophyte shows a normal morphological phenotype.

In one embodiment the *Secale* spp. infected with the fungal endophyte produces loline alkaloids and/or peramine.

In one embodiment the *Secale* spp. infected with the fungal endophyte has increased resistance to one or more pests or increased resistance to plant disease or both, as compared to *Secale* spp. that is not infected with a fungal endophyte.

In one embodiment the *Secale* spp. infected with the fungal endophyte has increased resistance to one or more pests, wherein the one or more pests are selected from the group consisting of: (1) species of aphids (Aphididae) represented by *Rhopalosiphum padi, Schizaphis graminum, Rhopalosiphum maidis, Metopoliphium dirhodum, Sitobion* spp., *Sitobion avenae, Sitobion fragariae, Diuraphis noxis*; (2) species of grass and cereal flies (Agromyzidae; Anthomyiidae, Chloropidae, Cephidae and Cecidomyiidae) represented by *Oscinella frit, Oscinella pusilla, Mayetiola destructor, Cerodontha* spp., *Cerodontha australis, Cerodontha angustipennis, Formia fumigata, Meromyze americana, Haplodiplosis marginata, Chlorops pumilionis, Tipula* spp. *Chromatomyia fuscula, Cephus pygmaeus, Chromatomyia fuscula, Contarinia tritici*; (3) species of thrips (Thripidae) represented by *Limothrips cerealium, Limothrips denticornis, Aptinothrips rufus, Stenothrips graminum*; (4) species of grasshoppers and crickets (Acrididae and Gryllidae) represented by *Locusta migratoria, Phaulacridium marginale, Phaulacridium. vittatum, Melanoplus* spp., *Teleogryllus commodus*; (5) species of bugs (Lygaeidae) represented by *Nyssius huttoni, Blissus leucopertus leucopertus*; (6) species of weevils (Curculionidae) represented by *Sphenophorus* spp.; (7) species of armyworm and cutworm (Noctuidae) represented by *Pseudaletia unipuncta, Spodoptera* spp., *Mythimna separata; Persectania aversa, Agrostis ipsilon*; (8) species of leaf beetles (Chysomelidae) represented by *Oulema melanopus*; (9) species of white grubs (Scarabaeidae) represented by *Popillia japonica, Costelytra zealandica, Phyllopertha* spp., *Rhizotrogus majalis, Anisoplia segetum*; (10) species of mealybug (Pseudococcidae and Coccidae) represented by *Phenacoccus hordei, Ba/anococcus poae, Ripersella rumicis, Porphyrophora tritici*; (11) species of wireworms (Elateridae) represented by *Conoderus* spp., *Limonius* spp.; species of beetles (Carabidae) represented by *Zabrus tenebrioides*; (13) species of mites (Eriophyidae and Penthaleidae) represented by *Penthaleus* spp., *Halotydeus destructor, Aceria* spp.; (14) species of stored product pests (Curculionidae, Silvanidae, Pyralidae, Gelechiidae, Tenebrionidae, Bostrichidae) represented by *Sitophilus oryzae, Sitophilus granarius, Sitotroga cerealella, Rhyzopertha dominica, Cryptolestes* spp., *Oryzaephilus surinamensis, Cadra cautella, Plodia interpunctella, Tribolium confusum, Tribolium castaneum, Lasioderma erricorne*; (15) species of froghopper (Cercopoidea) represented by *Philaenus spumarius* (16) species of nematodes represented by root lesion nematode (*Pratylenchus* spp., particularly *P. thomei, P. crenatus, P. neglectus* and *P. penetrans*), cereal cyst nematode (*Heterodera* spp. and *Punctodera* spp., particularly *H. avenae, H. latipons, H. hordecalis, H. filipjevi, H. mani, H. bifenestra, H. pakistanensis* and *P. punctata*), root knot nematode (*Meloidogyne* spp., particularly *M. chitwoodi, M. naasi, M. artiellia, M. microtyla, M. ottersoni, M. graminicola, M. graminis, M. kikuyensis* and *M. spartinae*), stem nematode (*Ditylenchus* spp., particularly *D. dipsicai* and *D. radicicola*); seed gall nematode (*Anguina tritici*); (16) species of slugs (*Deroceras reticulatum*, and *Arion* spp. particularly *A. hortensis* agg. and *A. subfuscus*). In one embodiment the pests are nematodes, preferably root lesion nematodes (*Pratylenchus* spp.), or leaf mining flies, *Cerodontha australis* (Diptera: Agromyzidae), also known as wheat sheath miner.

In one embodiment the *Secale* spp. infected with the fungal endophyte has increased resistance to plant disease, wherein the plant disease is caused by a plant pathogen selected from the group consisting of Barley yellow dwarf virus (Leteovirus), wheat soil-borne mosaic virus (Furovirus) and wheat streak mosaic virus (Tritimovirus), *Xanthomonas campestris, Pseudomonas syringae, Colletotrichum graminicola, Glomerella graminicola* [teleomorph], *Alternaria* spp., *Cladosporium herbarum, Mycosphaerella tassiana* [teleomorph], *Epicoccum* spp., *Sporobolomyces* spp., *Stemphylium* spp., *Bipolarlis sorokiniana, Cochliobolus sativus* [teleomorph], *Fusarium* spp., *Tilletia caries, Tilletia tritici, Tilletia laevis, Tilletia foetida, Hymenula cerealis, Cephalosporium gramineum, Helminthosporium sativum, Cochliobolus sativus* [teleomorph], *Coprinus sychromorbidus, Dilophospora alopecuri, Tilletia controversa, Claviceps purpurea, Sphacelia segetum* [anamorph], *Fusarium culmorum, Pseudoseptoria donacis, Selenophoma donacis, Neovossia indica, Tilletia indica, Puccinia recondita, Aecidium clematidis* [anamorph], *Cercosporidium graminis, Scolicotrichum graminis, Phaeosphaeria herpotrichoides, Leptosphaeria herpotrichoides, Ustilago tritici, Microdochium nivale, Fusarium nivale, Monographella nivalis* [teleomorph], *Erysiphe graminis, Pythium aphanidermatum, Pythium arrhenomanes, Pythium debaryanum, Pythium graminicola, Pythium ultimum, Gibberella zeae, Fusarium graminearum* [anamorph], *Septoria secalis, Septoria tritici, Mycosphaerella graminicola* [teleomorph], *Rhizoctonia cerealis, Rhizoctonia solani, Rhizoctonia zeae, Blumeria* spp., *Ceratobasidium cereale* [teleomorph], *Myriosclerotinia borealis, Sclerotinia borealis, Typhula idahoensis, Typhula incarnate, Typhula ishikariensis, Typhula ishikariensis* var. *canadensis, Stagonospora nodorum, Septoria nodorum, Phaeosphaeria nodorum* [teleomorph], *Leptosphaeria nodorum, Urocystis occulta, Puccinia graminis, Aspergillus* spp., *Nigrospora* spp., *Penicillium* spp., *Rhizopus* spp., *Pseudocercosporella herpotrichoides, Tapesia acuformis* [teleomorph], *Uredo glumarum* [anamorph], *Pyrenophora triticirepentis, Drechslera tritici-repentis* [anamorph], *Helminthosporium triticirepentis, Puccinia triticina, Pythium* spp., *Rhynchosporium secalis, Puccinia striiformis, Gaeumannomyces graminis* and *Fusarium pseudograminearum*.

Preferably the plant pathogen is *Puccinia recondita, Puccinia triticina, Puccinia graminis, Fusarium* spp., *Pythium* spp., *Rhynchosporium secalis, Puccinia striiformis, Gaeumannomyces graminis, Rhizoctonia solani* or *Fusarium pseudograminearum*.

In one embodiment, the *Secale* spp. infected with the fungal endophyte is selected from the group consisting of *Secale cereale, Secale montanum, Secale strictum, Secale sylvestre* and *Secale vavilovii*. Preferably the *Secale* spp. is *Secale cereale*.

In a third aspect the invention relates to a method of making a stable host plant/epichloae fungal endophyte combination comprising artificially infecting a *Secale* spp. plant with at least one fungal endophyte that forms a stable combination with the inoculated plant wherein the host plant shows no external symptoms of endophyte infection.

In one embodiment, the stable plant/fungal combination is sufficiently stable to allow vertical transmission of the endophyte. In one embodiment, vertical transmission is by tillers, particularly by floral tillers into seed, or by propagules. Preferably vertical transmission from a first generation of host plant to a second generation of host plant is by seeds.

In one embodiment, vertical transmission of the endophyte results in vertical transmission of the endophyte from a first generation to a second generation of host plants. Preferably vertical transmission from a first generation of host plant to a second generation of host plant is by seeds.

In one embodiment the method further comprises the step of selecting a *Secale* host plant showing no external symptoms of endophyte infection from a population of infected host plants.

In a fourth aspect the invention relates to a method of conferring at least some level of pest protection on a host *Secale* spp. plant comprising artificially infecting a *Secale* spp. plant with at least one epichloae fungal endophyte wherein the fungal endophyte-*Secale* plant combination produces at least one alkaloid at a level sufficient to confer at least some level of pest protection on the host plant.

In a fifth aspect, the invention relates to a method of conferring pest protection on a host *Secale* spp. plant comprising artificially infecting a *Secale* spp. plant with at least one epichloae fungal endophyte wherein the fungal endophyte-*Secale* plant combination produces at least one alkaloid that confers said pest protection on the host plant.

In one embodiment of the fourth or fifth aspects, the at least one alkaloid is an alkaloid selected from the group consisting of peramine, N-acetylnorloline, loline, N-formylloline, N-acetylloline, and N-methylloline.

In one embodiment of the fourth or fifth aspects, the at least one alkaloid is loline or peramine or both.

In one embodiment of the fourth or fifth aspects, the loline is produced at a level of at least 25 ug/g.

In one embodiment of the fourth or fifth aspects, the loline is produced at a level as shown in Table 7 for loline.

In one embodiment of the fourth or fifth aspects, the loline is produced in a range of at least 25 ug/g to about 3660 ug/g.

In one embodiment of the fourth or fifth aspects, the peramine is produced at a level of at least 1 ug/g.

In one embodiment of the fourth or fifth aspects, the peramine is produced at a level as shown in Table 7 for peramine.

In one embodiment of the fourth or fifth aspects, the peramine is produced in a range of at least 1 ug/g to about 45 ug/g.

In one embodiment the method further comprises the step of selecting a fungal endophyte-*Secale* plant combination that produces at least one alkaloid at a level sufficient to confer at least some level of pest protection on the host plant.

In a sixth aspect the invention relates to a *Secale* spp. seed infected with an epichloae fungal endophyte. Preferably the *Secale* spp. seed is a seed of a *Secale* spp. selected from the group consisting of *Secale cereale, Secale montanum, Secale strictum, Secale sylvestre* and *Secale vavilovii*. More preferably the seed is a seed of *Secale cereale*.

In one embodiment of any of the third, fourth, fifth or sixth aspects of the invention as set forth above, the *Secale* spp. is selected from the group consisting of *Secale cereale, Secale montanum, Secale strictum, Secale sylvestre* and *Secale vavilovii*. Preferably the *Secale* spp. is *Secale cereale*.

In one embodiment of any of the third, fourth, fifth or sixth aspects of the invention as set forth above, the at least one fungal endophyte is an endophyte isolated from *Elymus* spp.

Preferably the fungal endophyte is isolated from *Elymus mutabilis*. Preferably the fungal endophyte is an epichloae endophyte. Preferably the epichloae endophyte is selected from the group consisting of AR3039 (NRRL # 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073 (NRRL# 50721), AR3074 (NRRL# 50722), AR3076 (NRRL# 50723), and AR3078 (NRRL# 50724), and combinations thereof. Preferably the invention relates to strains AR3039, AR3046, AR3050, AR3067, AR3068, AR3074 and AR3078, preferably AR3046, AR3050 or AR3068.

Other aspects of the invention may become apparent from the following description which is given by way of example only and with reference to the accompanying drawings.

BRIEF DESCRIPTION OF THE DRAWINGS

The invention will now be described by way of example only and with reference to the drawings in which.

DETAILED DESCRIPTION OF THE INVENTION

Definitions

Figure 1:
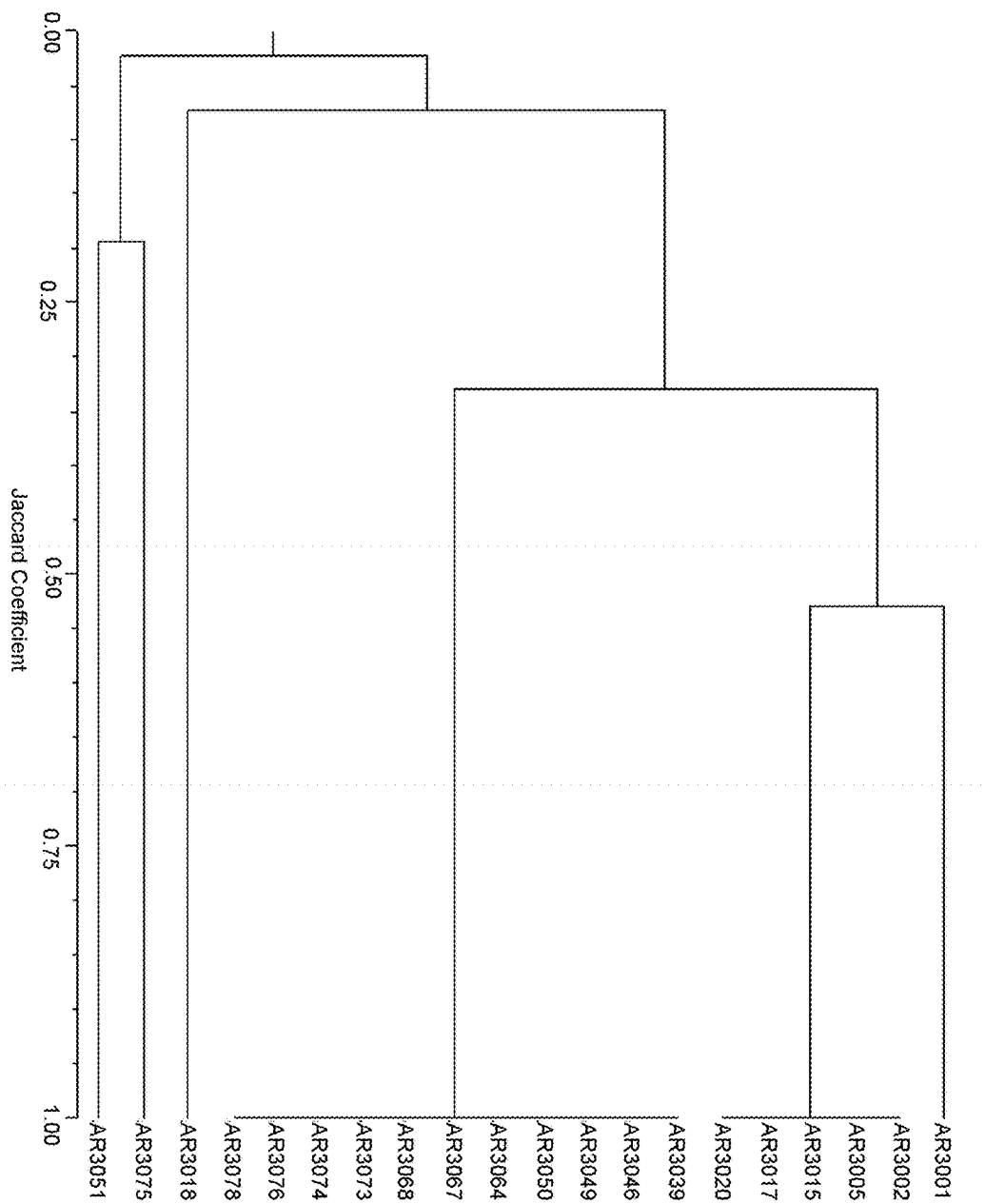
FIG. 1 shows a dendrogram of phylogenetic relationships based on SSR allele sizes as listed in table 2.

The following definitions are presented to better define the present invention and as a guide for those of ordinary skill in the art in the practice of the present invention.

Unless otherwise specified, all technical and scientific terms used herein are to be understood as having the same meanings as is understood by one of ordinary skill in the relevant art to which this disclosure pertains. Examples of definitions of common terms in botany, microbiology, molecular biology and biochemistry can be found in Biology of Plants, Raven et al. (eds.), W. H. Freeman and Company, (2005); Plant Physiology, Taiz et al. (eds.), Sinauer Associates, Incorporated, (2010); Botany: An Introduction to Plant Biology, J. D. Mauseth, Jones & Bartlett Learning, (2003); Methods for General and Molecular Microbiology, 3rd Edition, C. A. Reddy, et al. (eds.), ASM Press, (2008); Encyclopedia of Microbiology, 2nd ed., Joshua Lederburg, (ed.), Academic Press, (2000); Microbiology By Cliffs Notes, I. Edward Alcamo, Wiley, (1996); Dictionary of Microbiology and Molecular Biology, Singleton et al. (2d ed.) (1994); Biology of Microorganisms $11^{th}$ ed., Brock et al., Pearson Prentice Hall, (2006); Biodiversity of Fungi: Inventory and Monitoring Methods, Mueller et al., Academic Press, (2004); Genes IX, Benjamin Lewin, Jones & Bartlett Publishing, (2007); The Encyclopedia of Molecular Biology, Kendrew et al. (eds.), Blackwell Science Ltd., (1994); Molecular Biology and Biotechnology: a Comprehensive Desk Reference, Robert A. Meyers (ed.), VCH Publishers, Inc., (1995); Symbioses of grasses with seedborne fungal endophytes. Schardl C L et al. (2004) Annual Review of Plant Biology 55: 315-340; and Chemotype diversity of epichloae, fungal symbionts of grasses, Schardl C L, Young C A, Faulkner J R, Florea S, Pan J (2012) Fungal Ecology 331-344 (Schardl et al., 2012).

It is also believed that practice of the present invention can be performed using standard botanical, microbiological, molecular biology and biochemistry protocols and procedures as known in the art, and as described, for example in Methods of Studying Root Systems, vol. 33, Wolfgang Böhm, Springer-Verlag, (1979); Root methods: A Handbook, Albert L. Smit Springer, (2000); Biodiversity of Fungi: Inventory and Monitoring Methods, Mueller et al., Academic Press, (2004); Environmental Microbiology: Methods and Protocols, J. F. T. Spencer et al., Humana Press, (2004); Environmental Microbiology, P. D. Sharma, Alpha Science International, (2005); Environmental Microbiology, J. R. Leadbetter, Gulf Professional Publishing, (2005), Molecular Cloning: A Laboratory Manual, Maniatis et al., Cold Spring Harbor Laboratory Press, (1982); Molecular Cloning: A Laboratory Manual (2 ed.), Sambrook et al., Cold Spring Harbor Laboratory Press, (1989); Guide to Molecular Cloning Techniques Vol.152, S. L. Berger and A. R. Kimmerl (Eds.), Academic Press Inc., (1987); Biotechnology of Endophytic Fungi of Grasses. 1994 Bacon and White (Eds.), and other commonly available reference materials relevant in the art to which this disclosure pertains, and which are all incorporated by reference herein in their entireties.

The term "plant" as used herein encompasses whole plants and all parts of a plant from all stages of a plant lifecycle including but not limited to vegetative and reproductive cells and tissues, propagules, seeds, embryos, shoots, stems, leaves, leaf sheaths and blades, inflorescences, roots, anthers, ligules, palisade, mesophyll, epidermis, auricles, palea, lemma and tillers.

The term, "epichloae" as used herein refers to a collective group of fungal endophytes containing two genera of fungal endophytes: the members of the anamorphic form genus *Neotyphodium* and the members of the teleomorphic genus *Epichloë*.

The term, "epichloae endophyte" as used herein refers to an endophyte of the "epichloae" group that is known in the art, or has been shown herein, to form a symbiotic association with a host plant.

The term, "conferring at least some level of pest protection" as used herein encompasses measurably reducing the incidence, severity and/or duration of the effects of a pest on a *Secale* spp. plant. Preferably a measureable reduction is a statistically significant reduction with a P-value of 0.05 or less.

The term, "a level sufficient to confer pest protection" as used herein with reference to levels of alkaloids means any level of an alkaloid produced by the plant-endophyte symbiosis that is sufficient to produce a measureable reduction in of the incidence, severity or duration of a pest infestation infection or detrimental effect on a *Secale* spp. host plant that is infected with a fungal endophyte according to the invention. Preferably the alkaloid is peramine or loline or a loline derivative. Preferably a measureable reduction is a statistically significant reduction with a P-value of 0.05 or less.

The term "statistically significant" as used herein refers to the likelihood that a result or relationship is caused by something other than random chance. A result may be found to be statistically significant using statistical hypothesis testing as known and used in the art. Statistical hypothesis testing provides a "P-value" as known in the art, which represents the probability that the measured result is due to random chance alone. It is believed to be generally accepted in the art that levels of significance of 5% (0.05) or lower are considered to be statistically significant.

The term, "enhanced pest protection" as used herein refers to a level of pest protection conferred on a *Secale* spp. plant in symbiotic association with an epichloae fungal endophyte that reduces the incidence, severity and/or duration of a pest infestation, infection or detrimental effect on the plant due to the presence and/or activity of a given pest as compared to the incidence, severity and/or duration of the same pest infestation, infection and/or detrimental effect on a *Secale* spp. plant lacking a fungal endophyte (a control plant), and/or a *Secale* spp. plant having a different fungal endophyte.

The terms, "artificially infecting" and "artificial inoculation" as used herein encompass any inoculation of a plant, particularly a *Secale* spp. plant, particularly *Secale cereale*, with a fungal endophyte to form a plant/fungal symbiotic association that is not known from nature.

The term "in planta" as used herein in the context of fungal endophytes refers to the endophyte when it is living symbiotically within a host plant.

The term, "stable plant/fungal symbiosis" as used herein refers to a symbiotic association that persists throughout the lifecycle of the plant where the plant shows no external symptoms of endophyte infection. In a "stable symbiotic combination" the host plant is infected with the endophyte in a first generation and produces seeds which when germinated grow into a second generation of host plants that are also infected with the endophyte.

The term "normal life cycle" as used herein refers to the normal reproductive cycle of *Secale* which includes growth of a first generation of plant to produce seeds which when germinated grow into a second generation of plant.

The term "shows no external symptoms of endophyte infection" as used herein with reference to a host plant comprising a fungal endophyte means that the host plant has a substantially normal morphological phenotype as known in the art for that host plant. Wherein "substantially normal morphological phenotype" of a host plant as used herein refers to the typical morphology of the host plant as known and generally accepted in the art for that host plant for a given set of growth conditions.

The term "normal phenotype" of a host plant as used herein refers to the typical morphology, growth and other phenotypic characteristics of the host plant as displayed during the life cycle of the host plant, including the host plant reproductive cycle and host plant seed as known and generally accepted in the art for that host plant when not containing endophyte.

The term "abnormal phenotype" referring to a host plant as used herein refers to the morphology, growth or other phenotypic characteristics of the host plant at any stage of the host plant life cycle including the host plant reproductive cycle and host plant seed which is different from that known and generally accepted in the art as typical or within the generally observed range for that host plant. The term "abnormal phenotype" referring to a host plant as used herein may include stunted plants or dwarf plants or plants with obvious visual external evidence of endophyte infection or plants failing to complete normal reproduction through seed, but is not limited thereto.

The term "comprising" as used in this specification means "consisting at least in part of". When interpreting statements in this specification that include that term, the features, prefaced by that term in each statement, all need to be present but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Detailed Description

Many cool-season grasses (Poaceae, subfam. Pooideae) possess seedborne epichloae fungal endophytes that are known for their bioprotective properties, and especially for production of anti-pest alkaloids such as lolines (Zhang et al., 2010) and peramine (Koulman et al., 2007). Asexual epichloae (*Neotyphodium* species) are primarily or entirely transmitted vertically, whereas the sexual structures (stromata) of the related *Epichloë* species can give rise to horizontally transmissible spores (ascospores) (Zhang et al., 2010).

The majority of *Neotyphodium* species are considered closely related to species of the genus *Epichloë*. Many *Neotyphodium* species may have evolved from *Epichloë* by processes involving interspecific hybridization (Tsai et al., 1994). Based on molecular phylogenetic evidence, some authors consider that asexual *Neotyphodium* species are derived either from individual *Epichloë* species, or from hybrids sharing at least two ancestral *Epichloë* species (Tsai et al., 1994; Moon et al., 2004). Current taxonomy considers that the members of the anamorphic form genus *Neotyphodium* are very closely related members within the teleomorphic genus *Epichloë* (Glenn et al., 1996). Following previous codes of botanical nomenclature, a form genus refers to an asexual spore or vegetative state, and a teleomorphic genus refers to the sexual state. Currently the code of botanical nomenclature treats a single fungus with a single naming protocol (Miller et al. 2011). Collectively, the two genera, *Neotyphodium* and *Epichloë*, are known in the art as the "epichloae" endophytes.

Symbiotic associations between epichloae fungi and host grasses are common, and molecular phylogenetic evidence suggests that the species specificity observed in these symbiotic associations is due to the co-evolution of these groups of plants and fungal endophytes (Schardl et al., 2008).

No modern domesticated cereals are naturally infected with epichloae endophytes although some wild type relatives may be (Marshall et al., 1999).

Without wishing to be bound by theory, the inventors believe that during the evolution of modern cereals, agricultural practices such as storing seed may have led to the loss of historical associations if they existed (Welty et al., 1987).

Establishment of a stable plant/fungal symbiosis between an epichloae fungal endophyte and a host plant that is not a natural host for the fungus is both problematic and unpredictable (Simpson and Mace, 2012).

This is thought to be due to the requirement, in the formation of such symbioses, for successful integration of multiple biological variables between partners which can include ecological, biochemical and/or molecular incompatibilities (Christensen et al., 2000). The present disclosure details the large volume of research required, including significant trial and error experimentation, to develop successful protocols and procedures by which stable symbiotic associations between certain strains of epichloae fungal endophytes and *Secale* spp. host plants that are not the natural hosts for such fungi have been established.

Surprisingly, the inventors have determined that artificial inoculation can be used to establish stable plant/fungal symbioses between some epichloae fungal endophytes and *Secale* spp. host plants. Through the use of the inventive methods described herein, the inventors are able to produce infected *Secale* spp. host plants that form a stable symbiotic association with the infecting fungus that allows the infected plant to progress through a normal life cycle, and/or where the infected plant shows no external symptoms of endophyte infection. Additionally, the inventors have found that the establishment of such symbiotic associations can provide at least some level of benefit to the host plant in terms of the production in the plant of at least one loline alkaloid, loline alkaloid derivative, or peramine, or a combination thereof that may confer at least some level of pest protection to the host plant.

The inventors have surprisingly determined that certain fungal endophyte isolates taken from wild relatives of cereals are suitable for establishing stable plant/fungal symbioses with *Secale* spp. host plants, particularly *Secale cereale*. In particular, the inventors have established symbiotic associations that result in a fungal endophyte/*Secale* spp. host plant combination that may have at least some level of enhanced pest protection as compared to *Secale* spp. control plants; i.e., plants of the same *Secale* spp. that are un-infected with the same symbiotic epichloae fungal strain. Without wishing to be bound by theory, the inventors believe that enhanced pest protection is to be expected in fungal endophyte/host plant combinations that produce certain alkaloids, particularly loline, loline derivatives and/or peramine. Accordingly, the inventors believe that the production of loline and/or peramine alkaloid(s) by the epichloae fungal endophyte or the fungal endophyte/host plant combination provides at least some level of enhanced pest protection to the host plant. In particular, following from the use of the inventive endophyte strains and methods disclosed herein, the inventors have established that *Secale* spp. host plants, particularly *Secale cereale* host plants, infected with certain strains of epichloae fungal endophyte have enhanced protection against nematodes as compared to *Secale* control plants.

Generally speaking, symbiotic associations formed between host plants and their epichloae fungal endophytes are based on complex and intimate biological interactions which lead to a high degree of species specificity for both the endophyte and host (Simpson and Mace, 2012).

As a result of a lengthy research program, the applicants have identified for the first time, epichloae fungi capable of forming stable plant/fungal symbioses with *Secale* spp. host plants. The applicants have further identified endophytes capable of conferring to an infected host plant, when in symbiosis with *Secale* spp. host plants, particularly *Secale cereale* host plants, the ability to produce one or more alkaloids known to provide at least some level of enhanced pest protection to the plant, as compared to an un-infected control plant. In particular, the one or more alkaloids may be loline, loline derivatives or peramine alkaloids.

Accordingly, in one aspect the present invention relates to an isolated strain of epichloae fungal endophyte selected from the group consisting of AR3039 (NRRL# 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073 (NRRL# 50721), AR3074 (NRRL# 50722), AR3076 (NRRL# 50723), and AR3078 (NRRL# 50724), and combinations thereof. In one embodiment the isolated strain is biologically pure. Preferably the invention relates to strains AR3039, AR3046, AR3050, AR3067, AR3068, AR3074 and AR3078, preferably AR3046.

The above fungal endophyte strains were deposited at The United States Department of Agriculture, Agricultural Research Service Midwest Area, National Center for Agricultural Utilization Research, 1815 North University Street, Peoria, Ill., 61604-3902, USA on 13 Oct. 2011 for strains: AR3046 (NRRL# 50576), AR3049 (NRRL#50577), and AR3050 (NRRL# 50578), and on 6 Mar. 2012 for strains AR3039 (NRRL# 50716), AR3064 (NRRL# 50718), AR3067 (NRRL# 50719), AR3068 (NRRL# 50720), AR3073 (NRRL# 50721), AR3074 (NRRL# 50722), AR3076 (NRRL# 50723), and AR3078 (NRRL# 50724), according to the Budapest Treaty for purposes of patent procedure.

The endophytes were isolated from *Elymus* spp., including *E. mutabilis*, obtained from locations in Kyrgyzstan, Kazakhstan, the USSR and Russia as shown in Table 6.

The above endophytes were isolated from endophyte-infected *Elymus* spp., including *E. mutabilis*, plants following surface sterilisation of plant tissue as described (Christensen et al., 2002).

Once isolated, the isolated and/or biologically pure fungal endophyte may be cultured using standard techniques as known in the art and as disclosed herein, including in the examples.

In one embodiment, the fungal endophyte is cultured on antibiotic potato dextrose agar (ABPDA) between 20° C. and 25° C., preferably between 21° C. and 23° C. The optimal temperature for growth of the fungal endophyte is 22° C. Growth of the fungal endophyte at temperatures above or below this range may be possible although growth may be reduced or may cease entirely. In one embodiment, the fungal endophyte is cultured in the dark.

The invention also relates to a method of protecting a *Secale* spp. plant from pests comprising artificially infecting a *Secale* spp. plant with at least one epichloae fungal endophyte wherein the fungal endophyte in planta produces at least one alkaloid at a level sufficient to confer at least some level of pest protection to the host plant. In one embodiment the at least one alkaloid is an alkaloid selected from the group consisting of peramine, N-acetylnorloline, loline, N-formylloline, N-acetylloline and N-methylloline.

Inoculation may be carried out using *Secale* spp. seedlings that have been germinated for about two weeks. Preferably the seedlings have been germinated for 4 to 9 days.

Outside of this range, seedlings may still form effective associations but in some cases may be too young or too old for establishment of the fungal endophyte. Seeds need to be free of non-target fungi and bacteria to ensure that the seedlings are not overcome by microbial contamination.

In one embodiment, artificial inoculation may be carried out using basal inoculation of *Secale* spp. seedlings. To effectively establish the fungal symbiont/*Secale* spp. host plant association, inoculation of the endophyte should be made into the host plant meristem by incision of the plant and insertion of cultured fungal mycelium.

It is known to those familiar in the arts of natural pest resistance and protection of grasses that epichloae endophytes growing symbiotically with host grass plants may confer upon the combination some protection from pests. In particular it is known that loline alkaloids and the alkaloid peramine confer some such protection without notable or known toxicity to mammals or humans consuming the grass or products derived indirectly from consumption of the grass.

Lolines are a group of related bioactive natural products which share distinct chemical and biological characteristics. Lolines are alkaloids, i.e. organic compounds containing basic nitrogen atoms and are chemically defined as saturated 1-aminopyrrolizidines with an internal ether bridge joining two ring (C-2 to C-7) carbons. The internal ether bridge, which is uncommon in organic compounds, is considered a signature feature of the group. The specific lolines include norloline and derivatives of its 1-amino moiety being loline (with a methyl group), N-methylloline (with two methyl groups, NML), N-acetylnorloline (with an acetyl group, NANL), N-acetylloline (with a methyl group and an acetyl group, NAL) and N-formylloline (with a formyl group, NFL) (Schardl et al., 2007; Schardl et al., 2012).

Lolines are known to be generally pesticidal and pest-deterring compounds produced in grasses infected by endophytic epichloae fungal symbionts (*Epichloë/Neotyphodium* spp.). Lolines have been shown to increase resistance of the host grass plants to pest herbivory (Bush et al., 1997). The specific lolines may have some variations in the bioactivities against specific pests. It has also been suggested that the presence of lolines may provide a host plant with some level of protection from environmental stresses including drought and spatial competition (Malinowski and Belesky, 2000).

Loline alkaloids could be produced in the symbiotic combination by either the fungal endophyte or the host plant. What is important is the production of loline alkaloids by the combination, where the production is induced in the combination by the presence of the fungal endophyte on or within the plant tissues, particularly by the presence of fungal hyphae between plant cells. Historically, the reproduction of the conditions experienced in symbiosis to allow the production of loline alkaloids in vitro was found to be extremely difficult (Porter 1994). It was therefore unknown, until relatively recently, if the loline alkaloids observed to be produced in these symbiotic associations were produced by the fungal endophyte itself, or if they were synthesized in the plant in response to infection. Only relatively recent work by Blankenship et al. (2001) has demonstrated that the endophyte *Neotyphodium uncinatum* can produce lolines in chemically defined growth media. This work suggests that the endophyte is also the producer of the lolines in its naturally occurring host grass (Blankenship et al., 2001). Direct chemical analysis of naturally occurring epichloae also demonstrates this effect (Schardl et al., 2007).

Peramine (a pyrrolopyrazine alkaloid) is a bioactive alkaloid produced by some combinations of endophytes and plants (Schardl et al., 2012). Peramine production has been shown to be dependent upon the functioning of at least one gene of endophyte origin (Tanaka et al., 2005). Peramine has been shown to be a feeding deterrent of some insects which cause damage to plants and can confer protection against infestation of endophyte-infected plants by some insects (Rowan and Latch, 1994).

The invention further relates to a method of making a stable host plant/epichloae fungal endophyte combination comprising artificially infecting a *Secale* spp. plant with at least one fungal endophyte that forms a stable combination with the inoculated plant wherein the host plant shows no external symptoms of endophyte infection. This means that following the establishment of the combination the infected *Secale* spp. host plant exhibits a normal morphological phenotype for *Secale* spp. as known in the art, and as would be expected for the growth conditions where the combination is found.

Under certain conditions, fungal endophytes that are obligate symbionts of one host plant species or strain may be introduced to different host plant species or strain to form a combination that is not normally found in nature. However, such combinations can be unstable and result in host plants having an abnormal phenotype, i.e., abnormal morphological and/or physiological features as compared to host plants of the same strain or species that are either uninfected or that comprise a naturally occurring symbiont. Abnormal phenotypic features can include dwarf plants (Simpson and Mace, 2012), plants with conspicuous epiphytic growth (Christensen et al., 2012), vascular bundle colonisation (Christensen et al., 2001) and localised cell death (Christensen, 1995).

The applicant is the first to provide a stable symbiotic combination between *Secale* spp. host plants and epichloae fungal endophytes that results in a stable plant/fungal combination that shows no abnormal effects of endophyte infection. Stable symbiotic combinations provided herein can exhibit a normal morphological phenotype, and a complete and normal reproductive cycle.

In one embodiment, the stable symbiotic combination is sufficient to allow vertical transmission of the endophyte. In one embodiment, vertical transmission is by floral tillers and subsequently produced seeds. In one embodiment, vertical transmission of the endophyte is from a first generation to a second generation of host plants. Preferably vertical transmission from a first generation of host plant to a second generation of host plant is by seeds.

In one embodiment the host plant is a *Secale* spp. selected from the group consisting of *Secale cereale, Secale montanum, Secale strictum, Secale sylvestre* and *Secale vavilovii*. Preferably the host plant is *Secale cereale*.

The invention further relates to endophytes capable of conferring to a *Secale* spp. host plant upon infection, the ability for the endophyte/plant combination to produce one or more of loline, loline derivatives and/or peramine alkaloids.

The invention further relates to a seed of a *Secale* spp. plant that is infected with at least one epichloae fungal endophyte. Preferably the epichloae endophyte is isolated from *Elymus* spp. Preferably the fungal endophyte is isolated from *Elymus mutabilis*. Preferably the epichloae endophyte is selected from the group consisting of AR3039 (NRRL# 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073 (NRRL# 50721), AR3074 (NRRL# 50722), AR3076 (NRRL# 50723), and AR3078 (NRRL# 50724), and combinations thereof. Preferably the invention relates to strains AR3039, AR3046, AR3050, AR3067, AR3068, AR3074 and AR3078, preferably AR3046.

Preferably the *Secale* spp. seed is a *Secale cereale, Secale montanum, Secale strictum, Secale sylvestre* or *Secale vavilovii* seed. More preferably the seed is *Secale cereale* seed.

Various aspects of the invention will now be illustrated in non-limiting ways by reference to the following examples.

EXAMPLES

Example 1

Detection of Fungal Endophyte Strains

In excess of 580 accessions of seed of *Elymus* spp. were obtained from various sources and, where numbers of seed allowed, up to approximately 50 individual seed or seedlings were examined for infection with endophyte. Live endophyte in leaf sheaths of seedlings grown to the stage of two or more tillers was determined by the method of Simpson et al. (2012). Approximately 6% of accessions were shown to produce at least one seedling containing live endophyte which could be further examined as part of the following examples.

Example 2

Detection of Genetic Variation of Fungal Endophyte Strains

So as to focus upon selecting endophyte strains from those *Elymus* spp. containing live endophyte which could be of further interest the endophytes for up to 6 plants of each accession were partially characterised and distinguished for genetic variation by DNA 'fingerprinting' based on genotypic data derived from up to 8 selected simple sequence repeat (SSR) marker loci using primer sequences of Table 1. These primer sequences had previously been shown to generally amplify epichloae endophyte polymorphic DNA sequences from when the endophytes are in planta.

Samples of about 100 mg fresh weight of basal tiller were used to extract total genomic DNA (plant+endophyte), following the plant DNA isolation procedure of the FastDNA kit as recommended by the manufacturer (Bio 101, Vista, Calif.). SSR amplification was conducted with oligonucleotide primer pairs, using one of two polymerase chain reaction (PCR) protocols (Table 1). In both protocols PCR was carried out using an iCycler thermocycler (BioRad, Hercules, Calif., USA).

Protocol 1 was as described (Moon et al., 1999), except that an annealing temperature of 60° C. was used. In this protocol forward primers were labelled at the 5' terminus with the fluorophore 6-FAM™ (Applied Biosystems, Foster City, Calif.).

In Protocol 2 forward primers were synthesised with a 21 nucleotide M13 tail sequence at the 5'-terminus (5'-TG-TAAAACGACGGCCAGT-3') (SEQ ID NO: 1), to facilitate universal labelling of PCR products by a 6-FAM™-labelled M13 primer (Schuelke, 2000). Reverse primers were synthesised with the sequence 5'-GTTTCTT-3' (SEQ ID NO: 2) at the 5'-terminus end to promote non-templated adenylation at the 3'-terminus end of PCR product (Brownstein et al., 1996). A 10 μL PCR reaction volume was used, containing approximately 10 ng of total genomic DNA, 2.5 mM magnesium chloride, 1× PCR buffer, 0.05 mM of each dNTP, 0.0375 μM forward primer, 0.15 μM reverse primer, 0.15 μM of fluorescent-labelled M13 primer and 0.75 U of Platinum Taq DNA polymerase (Invitrogen, Carlsbad, Calif.). PCR was carried out using the following profile: (1) 94° C. for 4:00 minutes, (2) 30 cycles of: 94° C. for 30 seconds, 55° C. for 30 seconds and 72° C. for 30 seconds, (3) 8 cycles of: 94° C. for 30 seconds, 53° C. for 30 seconds and 72° C. for 30 seconds, (4) 72° C. for 30 minutes (after Schuelke 2000).

PCR products were analysed by capillary electrophoresis on an ABI 3100 Genetic Analyser using a 22 cm capillary array with POP-7™ polymer (Applied Biosystems). GS500 LIZ (Applied Biosystems) was used as an internal size standard. Electropherograms were analysed using ABI Prism GeneScan (v 3.7, Applied Biosystems), and genotype data was scored using ABI Prism Genotyper (v 3.7, Applied Biosystems).

Plants examined above were then further characterised by performing chemical analyses. Six infected seedlings were further examined for the presence of alkaloids, attributable to the presence of endophytes, such as indole diterpenes, ergot alkaloids, peramine and lolines. Representatives of each fungal genotype were sampled for more detailed genotyping using primers selected for polymorphic SSR loci.

Figure 2:
FIG. 2 shows four plants of *Secale cereale* cultivar Rahu; one uninfected (E−); and three infected with AR3046. From left to right: normal, dwarfed and stunted morphology. The E− and AR3046-infected normal and dwarf plants exhibit floral emergence, the stunted does not.

The results in table 2 and FIG. 2 show that the endophytes of this invention belong to a single clade designated Group 1 in table 2, and may be characterised as sharing at least most of the SSR allele sizes for the SSR loci listed in table 1 and table 2. Other endophytes of table 2, table 3 and FIG. 2 are examples for the purposes of illustrating the occurrence and relationships of different endophyte types which do not meet the requirements of this invention.

TABLE 1

SSR primer sequences.

| SSR | | Primer sequences (5'-3') | PCR protocol | SEQ ID NO: |
|---|---|---|---|---|
| B10 | forward | CGCTCAGGGCTA CATACACCATGG | 1 | 3 |
| | reverse | CTCATCGAGTAA CGCAGGCGACG | | 4 |
| ans019 | forward | TACCTCTGCACG GTGTATTCC | 2 | 5 |
| | reverse | TGCATAACACTC ACCTTATAGTCG | | 6 |
| ans033 | forward | GCGTTGAGGAGG CTAGATAGAA | 2 | 7 |
| | reverse | TTCCAAGCTGAA CAAAAGTCAA | | 8 |
| egs027 | forward | GATGACGTATCT TGATGCTACCAC | 2 | 9 |
| | reverse | CGTGTATAAAGT TCGGGATCCTAT | | 10 |
| egs031 | forward | GAGATATCCCGT CTCCTGATCTAA | 2 | 11 |
| | reverse | CACAGCGTTACA CTATCAACTTCC | | 12 |
| ces0004 | forward | CACTAAACACAC CCAAGAACAAGA | 2 | 13 |
| | reverse | AGACAGGTAAGA AGTTTTCCCCTT | | 14 |
| ces0022 | forward | AGCTTTCCAATG ACGACATACATA | 2 | 15 |
| | reverse | TAATTTAGGGTA GCATTTTCTCCG | | 16 |
| ces0041 | forward | GGTCCCTATTCT AATGCAGGTATG | 2 | 17 |
| | reverse | CAGTGTACGGGA CTTTGTCAATAC | | 18 |

TABLE 1-continued

SSR primer sequences.

| SSR | | Primer sequences (5'-3') | PCR protocol | SEQ ID NO: |
|---|---|---|---|---|
| ces0054 | forward | TGTATAATAAAC ATGGCGTGCTCT | 2 | 19 |
| | reverse | GTGTTGAAAGTT GTTGGATCACTC | | 20 |
| ces0060 | forward | CGAAATTGTAGA CTATGTTGGAGC | 2 | 21 |
| | reverse | GTAGATGTATTT TGAGCAGGGCTT | | 22 |
| ces0061 | forward | GAGTGAGACCCG GTGTAGTAAGTC | 2 | 23 |
| | reverse | GAGTCATTCTTC GTCCATTGTCTT | | 24 |
| ces0067 | forward | GAAATGAGGCGT CTATCTTAAAGC | 2 | 25 |
| | reverse | TTTCTTGATTTC CAAAGAACAACA | | 26 |
| ces0093 | forward | CTGCTAGACATA CTTGGAACATGG | 2 | 27 |
| | reverse | CAGTCGAATAAT TTAGGGAGCATT | | 28 |

TABLE 2

SSR allele sizes.

| | PCR product sizes (bp)[1,2] | | | | | |
|---|---|---|---|---|---|---|
| SSR | Group 1[3] | AR3001 | Group 2[4] | AR3018 | AR3075 | AR3051 |
| B10 | 159 185 | 188 | 188 | 171 | 181 195 | 193 |
| ans019 | 204 | 255 | 204 | 204 | 198 | 196 |
| ans033 | 176 | 179 | 181 | 176 | 183 193 | 193 |
| egs027 | 345 359 | 359 | 359 | 362 | 346 351 | 354 |
| egs031 | 259 283 | 259 | 259 | 280 | 308 | 308 |
| ces0004 | 185 | 185 | 185 | 174 | 179 187 | 187 |
| ces0022 | 204 209 | 209 | 209 | 211 | 204 | 206 |
| ces0041 | 247 257 | 261 | 261 | 250 | 254 | 266 |
| ces0054 | 261 | 261 | 261 | 267 | 255 280 | 280 |
| ces0060 | 238 250 | 238 | 238 | 239 | 246 257 | 233 246 |
| ces0061 | 154 177 | 154 | 162 | 154 | 164 221 | 152 |
| ces0067 | 277 281 | 275 | 277 | 265 | 271 295 | 298 |
| ces0093 | 143 145 | 145 | 145 | 149 | 143 | 143 |

[1]allele size +/− 0.5 bp
[2]For all SSR loci except B10, product size includes ca. 25 bp due to M13 and 'pig tail' sequences
[3]Group 1 = AR3039, 3046, 3049, 3050, 3064, 3067, 3068, 3073, 3074, 3076 and 3078
[4]Group 2 = AR3002, 3005, 3015, 3017 and 3020

Example 3

Isolation of Fungal Endophyte Strains

Fungus was isolated from a large number of endophyte-infected plants following surface sterilisation of plant tissue as generally known in the art, particularly as described by Christensen et al. (2002). Tillers were removed from plants by cutting at the base and trimming to about 5 cm before surface sterilising. Sectioned tillers were surface sterilised by quick rinse with 96% ethanol and a 1 minute soak in a 10% bleach solution followed by rinsing twice in sterile water. Tillers were sectioned transversely; sheath rings were separated and placed on to 5 µg/ml tetracycline antibiotic potato dextrose agar (ABPDA).

The Petri plates were incubated in the dark at 22-25° C. for 3-5 weeks. Cultures could be sub-cultured on the same medium.

Cultures were examined for colony growth rates, colony morphology, ability to produce conidia, size range of conidia, sequence of β-tubulin genes (tub2) (Moon et al. 2004) and other descriptive features all of which was taken into account for the selection of endophytes for further examination.

Selected cultures prepared and sometimes sub-cultured in the manner of this example were used for testing the inoculation and possible enduring infection of *Secale cereale* seedlings as described below.

Example 4

Endophyte Descriptions

In vitro characteristics when grown on PDA were consistent with descriptions of *Neotyphodium* (Christensen et al., 1993; Glenn et al., 1996), being slow to moderately slow growing, ranging after 4 weeks on PDA. Colonies raised from the agar, white, cottony, slightly to strongly convoluted, felty, with abundant aerial hyphae. Colony reverse tan to cream at margin. Conidiogenous cells were solitary, arising perpendicularly from the hyphae, wider at the base and tapering at the tip. Phialidic conidia were hyaline, smooth, navicular to lunate, 2.05-14.96 µm long×1.37-8.19 µm wide. None of the isolates were sterile. Individual characteristics per strain are listed in table 3.

TABLE 3

Conidial and colony dimensions

| Host | Endophyte | | Conidia (µm) | | | | | | Colony diameter (mm) | STDEV |
|---|---|---|---|---|---|---|---|---|---|---|
| | | | Av. length | | Av. width | Min Length | Max Length | Min width | Max width | | |
| *Elymus dahuricus* | AR | 3001 | 5.41 | x | 2.24 | 4.09 | 7.49 | 1.57 | 2.93 | 15.2 | 1.0 |
| *Elymus dahuricus* | AR | 3002 | 4.64 | x | 2.36 | 2.92 | 5.68 | 1.70 | 3.30 | 20.7 | 0.7 |
| *Elymus* sp. | AR | 3005 | 4.30 | x | 2.49 | 3.59 | 5.41 | 2.05 | 3.18 | 24.0 | 2.7 |
| *Elymus* sp. | AR | 3015 | 4.87 | x | 2.18 | 3.50 | 6.51 | 1.61 | 3.06 | 26.8 | 0.7 |
| *Elymus* sp. | AR | 3017 | 4.28 | x | 1.88 | 2.05 | 5.95 | 1.20 | 2.54 | 22.1 | 1.0 |
| *Elymus* sp. | AR | 3018 | 4.05 | x | 2.67 | 3.35 | 5.17 | 1.68 | 5.07 | 36.9 | 2.3 |
| *Elymus* sp. | AR | 3020 | 5.18 | x | 2.76 | 3.97 | 6.80 | 1.90 | 3.61 | 24.2 | 1.3 |
| *Elymus caninus* | AR | 3039 | 6.46 | x | 3.30 | 4.42 | 8.60 | 1.77 | 4.95 | 23.8 | 2.1 |
| *Elymus mutabilis* | AR | 3046 | 5.24 | x | 2.78 | 3.50 | 7.21 | 1.83 | 5.07 | 41.2 | 1.2 |
| *Elymus mutabilis* | AR | 3049 | 5.76 | x | 3.33 | 3.57 | 7.72 | 2.10 | 4.37 | 41.4 | 1.4 |
| *Elymus mutabilis* | AR | 3050 | 5.80 | x | 3.42 | 3.57 | 8.36 | 2.31 | 4.29 | 42.5 | 2.7 |
| *Elymus virginicus* | AR | 3051 | 3.91 | x | 2.40 | 2.74 | 5.10 | 1.37 | 3.16 | 93.2 | 4.8 |
| *Elymus mutabilis* | AR | 3064 | 12.18 | x | 6.54 | 8.11 | 14.96 | 4.54 | 8.19 | 23.0 | 5.4 |
| *Elymus uralensis* | AR | 3067 | 6.70 | x | 4.24 | 5.00 | 8.88 | 3.30 | 4.96 | 12.5 | 2.1 |
| *Elymus mutabilis* | AR | 3068 | 6.09 | x | 3.34 | 4.67 | 7.91 | 2.36 | 4.08 | 36.7 | 1.8 |
| *Elymus caninus* | AR | 3073 | 6.36 | x | 3.41 | 5.24 | 9.39 | 2.81 | 4.45 | 16.0 | 0.6 |
| *Elymus caninus* | AR | 3074 | 6.24 | x | 3.54 | 5.20 | 7.31 | 2.64 | 4.22 | 32.8 | 1.5 |
| *Elymus elymoides* ssp. *brevifolius* | AR | 3075 | 6.02 | x | 3.63 | 2.81 | 7.47 | 3.01 | 4.89 | 34.5 | 1.1 |
| *Elymus mutabilis* var. *oschensis* | AR | 3076 | 6.00 | x | 3.33 | 4.49 | 7.31 | 2.51 | 4.54 | 51.6 | 0.7 |

Example 5

Use of β-tubulin Gene Sequence to Determine Relationships of Endophytes to Known *Epichloë* species Fungal endophytes of grasses can be *Epichloë* species or *Neotyphodium* species. Some, but not all *Neotyphodium* species are apparently hybrids derived from two or more *Epichloë* species as disclosed primarily by comparing selected gene sequences (Moon et al., 2004).

The presence of multiple alleles for some of the loci used for SSR analysis of the endophytes (as in EXAMPLE 2 above) could indicate that clades to which they belong were likely to be of hybrid origin.

Gene sequences from tub2 of three examples of the endophytes, AR3039, AR3046 and AR3064 of this application were examined using minor variations of the method of Moon et al. (2004) for determination of likelihood of the endophytes being derived from one or more recognisable species of *Epichloë*. Four other endophytes of apparently different clades were also similarly examined to indicate their relationship to known *Epichloë* species.

The primers and conditions used for the PCR amplifications were modified so as to better ensure multiple alleles of tub2 were observable in all samples for which hybrid origins were considered likely or possible. The primer sequences selected were forward primer TCG GCC TCA CGA CGC ACA AC (RJ251-F) (SEQ ID NO: 29) and reverse primer CCC ATA CAT TAC ACC TTT CTG GCG (RJ252-R) (SEQ ID NO: 30) chosen so as to yield PCR products of endophytes from *Elymus* spp. corresponding substantially to and inclusive of the corresponding sequences reported and used for determination of relationships of *Epichloë* and *Neotyphodium* endophytes and their hybrids (Moon et al., 2004). The PCR was conducted with initial step of 95° (3 minutes); 35 cycles of 95° (30 seconds), 62° (30 seconds), 72° (45 seconds); final step 72° (5 minutes).

PCR products were sequenced by the method of Sanger (1997) on an ABI PRISM 3700 DNA Analyzer (Applied Biosystems). Sequences that contained multiple overlapping peaks were considered to have come from hybrids whereas those that did not were considered to have come from non-hybrids.

Cloning of PCR amplicons when more than one sequence was indicated was performed using the TOPO® TA Cloning® Kit (with pCR® 2.1-TOPO® Vector) (Invitrogen). Up to 10 clones were sequenced, as described above, and aligned using the Align X module of Vector NTI Advance 11 (Invitrogen), to sequences of individual tub2 alleles.

Individual tub2 alleles were assigned to the closest non-hybrid Epichloe species as follows: sequences were aligned using Dialign-TX (Subramanian et al., 2008), and maximum likelihood trees were built from this alignment using the Phylip software suite (Felsenstein, 2005). To create the final tree, the program DNAML was run, using 1,000 bootstraps and three randomizations of sequence input order per set, and condensed into a single consensus tree using the majority-rule approach. A tree was prepared using Dendroscope (Huson et al., 2007) for the closest attributions of known *Epichloë* species to selected endophytes.

The endophytes AR3039, AR3046 and AR3064 of this application yield two tub2 sequences consistent with the endophytes being hybrids of *E. bromicola* and *E. amarillans*. This is a hitherto unreported hybrid and may be considered a new species which is for the present designated *E. bromicola* x *amarillans*.

Endophyte strains AR3049, AR3050, AR3067, AR3068, AR3073, AR3074, and AR3078 group closely with AR3039, AR3046 and AR3064 by SSR analysis (FIG. 1) and may also be considered most likely to be of *E. bromicola* x *amarillans*. Three of the other endophytes in comparative testing were considered to group with just *E. bromicola* and one other endophyte with *E. yangzii*, these being representative of other groups of endophytes with shared patterns of SSR genotypes observed from *Elymus* spp. sources.

Taken together the SSR and β-tubulin data suggest that the endophyte strains AR3039, AR3046, AR3049, AR3050, AR3064, AR3067, AR3068, AR3073, AR3074, and AR3078 form a representative group of newly characterized endophytes that can be considered a functional clade that can be transferred from their native host plant to the alternate host, *Secale*, resulting an artificially created stable symbiotic *Secale*/endophyte combination wherein the infected *Secale* host exhibits normal growth and has a normal life cycle.

Example 6

Inoculation of Epichloae Fungal Endophytes into *Secale cereale*

Seeds of *Secale cereale*, cultivars Rahu, Amilo, and "KWS", and selections of *S. cereale* cultivars obtained from Dr Mark Newell, The Samuel Roberts Noble Foundation (NF95307A, NF95319B, 97326, Bates RS4, or MATON2) were surface sterilised and inoculated as described by Latch and Christensen (1985). Seeds were surface sterilised by immersion in a 50% sulphuric acid solution for 15 minutes followed by a five times rinse with tap water and immersion in a 10% domestic bleach (Janola) solution for 15 minutes followed by two rinses in sterile water. Seeds were dried in a laminar flow cabinet on sterile Whatmann filter paper before arranging on 4% water agar Petri plates. The seeds on plates were germinated in the dark at 22-25° C. for 4-9 days and resulting etiolated seedlings were inoculated before being returned to the dark incubator for 7 days. Following this incubation plates were placed under white fluorescent lights for at least 7 days before removing seedlings and planting them in commercial potting mix and growing them in a glasshouse. Plants were grown for ca. 6 weeks before identifying infected individuals. Infected plants were identified by the method of Simpson et al. (2012). Plants were further grown in a glasshouse to examine the plant phenotype of infected plants in comparison with the typical uninfected plants and in particular to determine whether inflorescences and seed heads would be formed.

A summary of successful inoculations marked with "yes" is included in Table 4 for those endophyte strains where at least some of the inoculated plants were of substantially normal phenotype and were able to progress through a normal life cycle (FIG. 2). Seeds were collected from the plants as indicated in Table 4.

TABLE 4

Strains inoculated into and infecting *S. cereale* and examples of seed production.

| Endophyte | Inoculation of Secale attempted | Infected plants of Secale obtained | Infected plants of Secale produced seed | Seed of Secale was infected with endophyte | Seed was infected with viable endophyte |
|---|---|---|---|---|---|
| AR3039* | Yes | Yes | Yes | Yes | Yes |
| AR3046* | Yes | Yes | Yes | Yes | Yes |
| AR3039** | Yes | Yes | Yes | TBD | TBD |
| AR3046/** | Yes | Yes | Yes | TBD | TBD |
| AR3046/NF95307A*** | Yes | Yes | Yes | TBD | TBD |
| AR3046/NF95319B*** | Yes | Yes | Yes | TBD | TBD |
| AR3046/97326*** | Yes | Yes | Yes | TBD | TBD |
| AR3046/Bates RS4*** | Yes | Yes | Yes | TBD | TBD |
| AR3046/MATON2*** | Yes | Yes | Yes | TBD | TBD |
| AR3049* | Yes | Yes | Yes | Yes | Yes |
| AR3050* | Yes | Yes | Yes | Yes | Yes |
| AR3064* | Yes | Yes | Yes | Yes | Yes |
| AR3067* | Yes | Yes | Yes | Yes | Yes |
| AR3068* | Yes | Yes | Yes | Yes | Yes |
| AR3068**** | Yes[1] | Yes[1] | Yes[1] | TBD | TBD |
| AR3073* | Yes | Yes | Yes | yes | Yes |
| AR3074* | Yes | Yes | Yes | Yes | Yes |
| AR3076* | Yes | Yes | Yes | Yes | Yes |
| AR3078* | Yes | Yes | Yes | Yes | Yes |

*inoculated into *S. cereale* var. Rahu
**inoculated into *S. cereale* var. Amilo
***inoculated selections of rye (*Secale cereale*) ex Dr Mark Newell, The Samuel Roberts Noble Foundation.
Variant as indicated: NF95307A, NF95319B, 97326, Bates RS4, or MATON2.
TBD = to be determined
Yes[1] = anticipated result Example 7

Alkaloid Production in Endophyte Infected Natural Parent Plants

Leaf blades and pseudostems of *Elymus mutabilis, Elymus caninus, Elymus uralensis, Elymus nevskii* and *Elymus mutabilis* var. *oschensis* plants infected with particular endophyte strains were analysed for loline alkaloids and peramine by minor modifications of established methods (Kennedy and Bush, 1983; Yates et al., 1989) and peramine (Rasmussen et al., 2012). The results are shown in Table 5. The total amount of loline alkaloids was greater in the leaves of the examined plants than in the pseudostems. Without wishing to be bound by theory, the inventors believe that the total amounts of alkaloids present in the examined plants are representative of a range that is sufficient to provide at least some pest protection to the host plant (Wilkinson et al., 2000). These results show that a number of endophyte strains within the clade defined by the SSR and β-tubulin data presented elsewhere herein, when in planta, may confer upon the symbiotic combination a capacity to produce measurable amounts of loline alkaloids or peramine or both.

TABLE 5

Total lolines and peramine alkaloids for endophyte-infected parent *Elymus* plants.

| Endophyte | Plant part | Lolines[1] (µg/g) | Peramine[2] (µg/g) |
|---|---|---|---|
| AR3039 | Leaf blade | 56 | 55.6 |
| | Pseudostem | 34 | 26.1 |
| AR3046 | Leaf blade | 461 | 78.4 |
| | Pseudostem | 240 | 45.2 |
| AR3049 | Leaf blade | 437 | 83.4 |
| | Pseudostem | 242 | 45.5 |
| AR3050 | Leaf blade | 532 | 84.7 |
| | Pseudostem | 379 | 59.2 |
| AR3064 | Leaf blade | 465 | 66.0 |
| | Pseudostem | 342 | 39.0 |
| AR3067 | Leaf blade | 205 | 27.5 |
| | Pseudostem | 107 | 16.3 |
| AR3068 | Leaf blade | 372 | 59.4 |
| | Pseudostem | 151 | 31.1 |
| AR3073 | Leaf blade | 43 | 65.8 |
| | Pseudostem | 34 | 24.8 |
| AR3074 | Leaf blade | 257 | 47.5 |
| | Pseudostem | 169 | 32.9 |
| AR3076 | Leaf blade | 312 | 53.2 |
| | Pseudostem | 151 | 28.3 |
| AR3078 | Leaf blade | 466 | 32.7 |
| | Pseudostem | 273 | 30.9 |

Footnote:
[1]analysed by GC-FID,
[2]analysed by LC-MS

Example 8

Source and Geographic Origin of Selected Endophytes from *Elymus* spp.

Table 6 lists a number of isolated endophyte strains disclosed herein, the source accession numbers from which they were obtained, the putative species of the original host plant accession, and the regional source of the accession. The *Elymus* spp. host plants were generally obtained from central Asia.

TABLE 6

Strains of isolated endophytes by AR code number, original putative host species, regional source, and source accession number.

| Endophyte | *Elymus* Host | Region | | Source of accession |
|---|---|---|---|---|
| AR3039 | E. caninus | not known | RBG[1] | 0006334 |
| AR3046 | E. mutabilis | Lake Issyk Kul, Kyrgyzstan | PI[2] | 564954 |
| AR3049 | E. mutabilis | Lake Issyk Kul, Kyrgyzstan | PI | 564954 |
| AR3050 | E. mutabilis | Lake Issyk Kul, Kyrgyzstan | PI | 564954 |
| AR3064 | E. mutabilis | Gorno Altay, Russia | PI | 564949 |
| AR3067 | E. uralensis | Amla Ata, Kazakhstan | PI | 547365 |
| AR3068 | E. mutabilis | USSR | NGB[3] | 90498 |
| AR3073 | E. caninus | not known | RBG | 0006334 |
| AR3074 | E. caninus | Cheketeman Pass, Gorno Altay, Russia | PI | 564915 |
| AR3076 | E. mutabilis var. oschensis | Khigiz-Alatau mountains, Kyrgyzstan | PI | 531640 |
| AR3078 | E. nevskii | Novosibirsk, Russia | PI | 564925 |

Footnotes
[1]Royal Botanic Gardens, Seed Conservation Department, Ardingly, UK
[2]Pullman Institute, Washington State University, Pullman, WA., USA
[3]Nordic Genetic Resource Centre (NordGen), Alnarp, Sweden

Example 9

Alkaloid Production in *Secale cereale* Plants

Seedlings of *Secale cereale* cultivar Rahu were inoculated with endophytes as listed in Table 7, grown in a glasshouse and confirmed as containing endophyte with a substantially normal plant phenotype. Leaf blades and stems separately were analysed for loline alkaloids (Kennedy and Bush, 1983; Yates et al., 1989) or peramine (Garthwaite et al., 1994). The results in Table 7 show concentration ranges for both loline alkaloids and peramine. Without wishing to be bound by theory, the inventors believe that the total amounts of loline alkaloids and peramine present in the examined plants are representative of a range that is sufficient to provide at least some pest protection to the host plant (Rowan 1993; Wilkinson et al., 2000; Bacetty et al., 2009a 2009b).

TABLE 7

Alkaloid analysis observations of *S. cereale* plants (up to 3 plants) infected with endophytes.

| | Plant part | Lolines[1] (µg/g) | | | Peramine[2] (µg/g) | | |
|---|---|---|---|---|---|---|---|
| Endophyte | Rahu | n | Mean | Range | n | Mean | Range |
| AR3039 | Leaf blade | 6 | 97 | 54-193 | 6 | 23.3 | 18.1-33.0 |
| | Stem | 6 | 87 | 65-110 | 6 | 16.7 | 11.6-21.1 |
| AR3046 | Leaf blade | 5 | 1487 | 911-3285 | 3 | 18.7 | 14.1-23.2 |
| | Stem | 4 | 250 | 167-280 | 3 | 15.6 | 15.1-16.0 |
| AR3049 | Leaf blade | 6 | 1765 | 642-3660 | 4 | 25.2 | 17.0-30.1 |
| | Stem | 6 | 362 | 250-669 | 2 | 16.2 | 12.1-20.3 |
| AR3050 | Leaf blade | 1 | 1607 | — | 1 | 16.8 | — |
| | Stem | 1 | 342 | — | 5 | 6.8 | 4.3-12.4 |
| AR3064 | Leaf blade | 4 | 358 | 140-490 | 3 | 7.3 | 1.6-11.4 |
| | Stem | 4 | 103 | 32-172 | 2 | 4.0 | 1.2-6.9 |
| AR3067 | Leaf blade | 4 | 111 | 101-119 | 1 | 47.7 | — |
| | Stem | 2 | 136 | 136-136 | 1 | 36.3 | — |
| AR3068 | Leaf blade | 6 | 1108 | 895-1696 | 5 | 21.0 | 11.6-30.2 |
| | Stem | 6 | 276 | 122-488 | 2 | 15.2 | 5.8-24.5 |

TABLE 7-continued

Alkaloid analysis observations of *S. cereale* plants (up to 3 plants) infected with endophytes.

| | Plant part | Lolines[1] (µg/g) | | | Peramine[2] (µg/g) | | |
|---|---|---|---|---|---|---|---|
| Endophyte | Rahu | n | Mean | Range | n | Mean | Range |
| AR3073 | Leaf blade | 6 | 86 | 56-112 | 6 | 20.8 | 11.1-38.3 |
| | Stem | 5 | 62 | 40-82 | 3 | 25.0 | 16.9-36.1 |
| AR3074 | Leaf blade | 2 | 599 | 275-922 | 2 | 14.4 | 8.0-20.7 |
| | Stem | 2 | 431 | 392-470 | 4 | 3.5 | 2.5-5.2 |
| AR3076 | Leaf blade | 3 | 310 | 164-588 | 4 | 14.9 | 7.3-18.7 |
| | Stem | 3 | 230 | 92-437 | 3 | 13.7 | 11.4-16.4 |
| AR3078 | Leaf blade | 5 | 489 | 54-1646 | 5 | 15.8 | 1.4-43.4 |
| | Stem | 5 | 219 | 39-607 | 4 | 11.5 | 3.6-24.0 |

Footnote:
[1]analysed by GC-FID,
[2]analysed by ELISA

Example 10

*Elymus mutabilis*/Endophyte Combinations having Bioactivity Against Cereal Pests In the absence of endophyte-free *E. mutabilis* controls, meadow fescue with and without its natural endophyte (*Neotyphodium uncinatum*) has been used because it is known to produce loline alkaloids and has known activity against aphids.

Effect on Aphids

The aphid *Rhopalosiphum padi* is a significant pest of cereal plants because it transmits barley yellow dwarf virus.

In a choice bioassay carried out using tillers in Petri dishes, numbers of *Rhopalosiphum padi* on *Elymus mutabilis* infected with AR3050 were similar to numbers on meadow fescue infected with its natural endophyte *Neotyphodium uncinatum* and significantly less than the number of aphids on the meadow fescue endophyte-free control (Table 8).

TABLE 8

Number of *R. padi* aphids found on tillers of *E. mutabilis* infected with AR3050 and meadow fescue with (MF E+) and without (MF E−) its natural endophyte *N. uncinatum* in a choice trial over 3 days.

| Endophyte treatment | No. aphids/tiller | | |
|---|---|---|---|
| | Day 1 | Day 2 | Day 3 |
| AR3050 | 2.8 | 1 | 1.5 |
| MF E+ | 0 | 0 | 0.8 |
| MF E− | 5.2 | 7.5 | 15.3 |
| P-value | 0.003 | <0.001 | <0.001 |

The results of this trial suggest that loline alkaloids produced as a result of the symbiotic association formed between *E. mutabilis* and AR3050 may deter aphid grazing as seen in pasture grasses (Wilkinson et al., 2000).

Effect on Aceria Mites

*Aceria* spp., notably *A. tosichella*, are mites which transmit the wheat streak mosaic virus in Australia. The mite used in these trials has been identified as of *Aceria* spp., tentatively as *A. tosichella*.

Because of the lack of *E. mutabilis* controls without endophyte and the unknown effect of plant genotype on the occurrence of *Aceria* mites the effects of loline alkaloids on mites was assessed on six endophyte-infected and six endophyte-free meadow fescue plants. *Aceria* mites were counted on three tillers of each plant. Significantly more mites occurred on endophyte free plants than endophyte-infected (No./tiller: 74 for E+ cf 454 for E-. P<0.001). The results are given below in Table 9.

TABLE 9

Average number of *Aceria* mites on two leaves of three tillers on six meadow fescue plants with (E+) and without (E-) the endophyte *N. uncinatum*.

|  | E+ | E- | SED | Significance |
|---|---|---|---|---|
| Tiller 1 | 65 | 417 | 70.6 | <0.001 |
| Tiller 2 | 101 | 543 | 97.5 | 0.001 |
| Tiller 3 | 59 | 403 | 57.1 | <0.001 |
| All | 224 | 1363 | 134.2 | <0.001 |

As shown above in the applied trial, the results in this mite trial suggest that loline alkaloids are responsible for deterring mite grazers, similar to the effects on aphids that have been shown in pasture grasses (Wilkinson et al., 2000).

Effect on Light Brown Apple Moth

This insect has known sensitivity to bioactives produced by endophytes in ryegrass. It has been used here to indicate the presence of bioactives in *E. mutabilis* plants infected with AR3046.

A severe effect of AR3046 was found when *E. mutabilis* plant material taken from plants infected with AR3046 was incorporated into an artificial diet and fed to light brown apple moth. The average percentage of larvae which established and commenced feeding within the first 24 hours of placement of neonate larvae on the tested diets was: 88% for the average of three other *Elymus* species not infected with endophyte, as compared to 4% for larvae whose diet contained *E. mutabilis* infected with AR3046. By Day 10 of the trial, 60% of the larvae fed endophyte-free plant material had moulted to the first instar as compared to only 13% of those being fed AR3046 moulting to instar. The results of this trial are given below in Table 10.

TABLE 10

Proportion of light brown apple moth that had established on diets after 24 h and commenced feeding after 24 and 48 h, and the average time to the first moult when placed on diets incorporating freeze dried plant material from *Elymus* without endophyte or infected with the loline-producing endophyte AR3046.

| | | Proportion Established | Proportion Feeding | | Time to 1$^{st}$ moult |
|---|---|---|---|---|---|
| Plant | Endophyte | 24 h | 24 h | 48 h | Ln days |
| *Elymus* sp. | Nil | 0.91 | 0.83 | 0.87 | 2.176 |
| *Elymus mutabilis* | AR3046 | 0.05 | 0.05 | 0.00 | 2.716 |
| SED | | 0.153 | 0.102 | 0.129 | 0.1079 |
| P | | <0.001 | <0.001 | <0.001 | <0.001 |

The results in this moth trial strongly suggest that AR3046 produces loline alkaloids that are responsible for deterring light brown apple moth grazers.

Example 11

Pest Protection in Endophyte Infected *Secale*

An experiment was done to test the ability of endophyte to protect *Secale* from root lesion nematodes (*Pratylenchus* spp.) using tillers of *Secale cereale* cultivar Rahu, with or without AR3046 endophyte. Eleven individual tillers of E+ and E- Rahu, selected from 4 independent parent plants per treatment (2-3 clones per parent plant) were transplanted into 5×5×12 cm deep root trainers containing 100 g field collected soil with a natural infestation of 30 *Pratylenchus* spp. per 100 g. An additional 30 laboratory reared *Pratylenchus penetrans* were added to each root trainer such that each plant was exposed to 60 nematodes. Plants were incubated in an illuminated growth cabinet at 20° C. for 30 days. Plants were then removed from the soil, the roots washed, then cleared using 1.5% sodium chloride for 3 minutes. Nematodes within the roots were stained using aniline blue in glycerol. Roots were then examined under a microscope and numbers of nematodes within root systems counted. Endophyte infection did not influence root weight.

Presence of AR3046 endophyte caused a significant (P<0.05) reduction in numbers of nematodes per root system (Table 11).

As shown in the insect deterrent trials described above, the results in this nematode trial strongly suggest that the loline alkaloids produced by AR3046 are responsible for conferring at least some level of pest protection on infected *Secale* by deterring nematode colonization of the roots of endophyte infected *Secale* plants. This is consistent with lolines being shown to have deterrent and pesticidal effects with nematodes (Bacetty et al., 2009a 2009b).

TABLE 11

Number of root lesion nematodes (*Pratylenchus* spp.) in roots of *Secale cereale* cultivar Rahu plants with endophyte (AR3046) and without endophyte (E-) (P = 0.013).

| Endophyte | Number of nematodes per plant |
|---|---|
| AR3046 | 3.4 |
| E- | 8.1 |

Example 12

Effects of *Secale cereale* var. "Rahu" Infected with Endophyte AR3046 on *Cerodontha australis*

Grasses and cereals in New Zealand and Australia are frequently infested by larvae of a leaf mining fly, *Cerodontha australis* (Diptera: Agromyzidae), also known as wheat sheath miner. Larvae of this fly feed internally on the tissues of a range of grasses and cereals, causing damage that can result in tiller death. The mines leave a visible trail in the leaves. In this experiment, *S. cereale* cv. Rahu plants infected with a loline-producing endophyte, AR3046, or uninfected (Nil) were exposed to infestations by *C. australis*. Meadow fescue infected with its natural endophyte *Neotyphodium uncinatum* was included in the experiment because this endophyte also produces loline alkaloids.

Method

Six plants each of "Rahu" *Secale* infected with AR3046 and meadow fescue infected with *N. uncinatum*, with their endophyte-free counterparts (Nil) were compared for their effects on infestations by *C. australis*. Plants were randomly arranged within replicate groups comprised of a single plant of each treatment and four leaf-miner fly pupae dissected from perennial ryegrass plants growing in a screenhouse were placed at the base of each plant (in amongst the tillers). In addition, one female and one male adult fly that had already emerged from collected pupae were released onto replicate groups 1-5 and one male onto replicate group 6. Each replicate group of four plants was covered with fine net cloth placed over a wire cage. Cages were removed from the plants 2 weeks after they were set up. The experiment was undertaken in a glasshouse with a maximum daily temperature of 22° C. and plants were watered by hand as necessary.

Tiller numbers, and the number and length of larval mines in each leaf were recorded 4 and 6 weeks after pupae and adults were placed on plants and the presence of larval damage or pupae in each stem at 6 weeks.

Count data were log transformed (ln) and the proportional data square root transformed before analysis in Genstat v16 by ANOVA blocked by replicate.

Results

Only one of the six Rahu plants infected with AR3046 was infested with flies compared with all of the six Rahu Nil plants. There were significantly fewer tillers/plant (P<0.001) and a lower proportion of tillers (P<0.002) infested by *C. australis* on Rahu infected with AR3046 than Rahu Nil at both the 4 and 6 week checks (Table 12). In addition AR3046 reduced the number of mines/plant (P<0.001) (mines are vertical trails left by larvae as they feed inside the plant tissues) and the number of tiller stems (i.e. the lower part of the each tiller) that were damaged by or contained larvae or pupae.

Generally the meadow fescue plants were more heavily infested by flies with all plants attacked. Infection by *N. uncinatum* in meadow fescue reduced the proportion of tillers infested with *C. australis* at 4 (P<0.007) and at 6 weeks (P<0.002) (Table 12). In addition, significantly fewer (P<0.05) tiller stems were damaged or contained larvae in endophyte-infected than in endophyte-free meadow fescue.

being shown to have deterrent and pesticidal effects with other insects and plant pests (Schardl et. al., 2007; Bacetty et al., 2009a 2009b).

Example 13

Effects of "Rahu" *Secale* Infected with Endophyte AR3046 on Spittle Bugs

An experiment was carried out comparing the effects of *Secale cereale* var. Rahu infected with AR3046 and meadow fescue infected with its natural loline-producing endophyte *N. uncinatum*, together with respective uninfected controls, on a xylem feeding insect pest *Philaenus spumarius* (spittle bug) which is believed to sensitive to loline alkaloids. Plants were cloned so that for each experiment with the different insects, six genetically identical plants of infected Rahu and infected and uninfected meadow fescue were used but only three of the six Rahu endophyte-free plants were the same.

Two experiments were carried out, the first using mature spittle bug nymphs which developed to adults quite quickly and the second using younger nymphs. In both cases three spittle bugs were released onto each plant. In the first experiment the plants were covered with acetate cages that were not completely insect proof whereas in the second experiment insect-proof nylon covers were used. The number of spittle bug present and the number of small, medium and large 'gobs' of spit, which spittle bugs excrete as they feed, was counted regularly during each experiment. Rahu

TABLE 12

The mean number of live tillers, number of damaged tillers, proportion of damaged tillers and number of mines/plant caused by *Cerodontha australis* 4 and 6 weeks after pupae and adults were released on plants of *Secale cereale* var. "Rahu" and meadow fescue with (MF *N. unc.*) and without (MF Nil) endophyte are tabulated below. The mean number of tillers with damage and or pupae in the stem of tillers is given for the 6 week check. Data for mean numbers are log (ln) transformed and proportional data are square root transformed.

|  | Rahu AR3046 | Rahu Nil | MF *N unc.* | MF Nil | SED[1] | Rahu[2] P-value | MF[2] P-value |
|---|---|---|---|---|---|---|---|
| 4 Weeks |  |  |  |  |  |  |  |
| No. live tillers/plant | 4.04 | 3.01 | 3.89 | 3.35 | 0.309 | 0.005 | 0.103 |
| No. damaged tillers/plant | −0.33 | 1.43 | 2.37 | 2.73 | 0.365 | <.001 | 0.349 |
| Propn. damaged tillers | 0.04 | 0.45 | 0.58 | 0.93 | 0.113 | 0.002 | 0.007 |
| No. mines/plant | −0.33 | 1.64 | 2.56 | 3.26 | 0.370 | <.001 | 0.077 |
| 6 Weeks |  |  |  |  |  |  |  |
| No. live tillers/plant | 3.67 | 3.15 | 3.88 | 3.33 | 0.309 | 0.114 | 0.092 |
| No. damaged tillers/plant | −0.69 | 1.82 | 2.50 | 2.92 | 0.332 | <.001 | 0.222 |
| Propn. damaged tillers | 0.00 | 0.53 | 0.62 | 1.03 | 0.106 | <.001 | 0.002 |
| No. mines/ plant | −0.69 | 2.24 | 2.71 | 3.35 | 0.330 | <.001 | 0.075 |
| No. tillers with stem damage | −0.69 | 1.55 | 1.66 | 2.52 | 0.396 | <.001 | 0.046 |

[1]SED = standard error of the difference for comparisons of all four treatments
[2]P values are for comparisons between infected and endophyte-free plants within species Conclusion Infection of *Secale* cv. Rahu infected with the loline-producing endophyte, AR3046, significantly reduced infestations of the leaf mining fly *Cerodontha australis*. Another loline-producing species of endophyte in meadow fescue also reduced the proportion of tillers damaged by fly larvae and the number of tillers with stem damage.

The results in this trial strongly suggest that the loline alkaloids produced by AR3046 are responsible for conferring at least some level of pest protection on infected *Secale* spp. by reducing infestations of *C. australis* on endophyte infected *Secale* spp. plants. This is consistent with lolines

Figure 3:
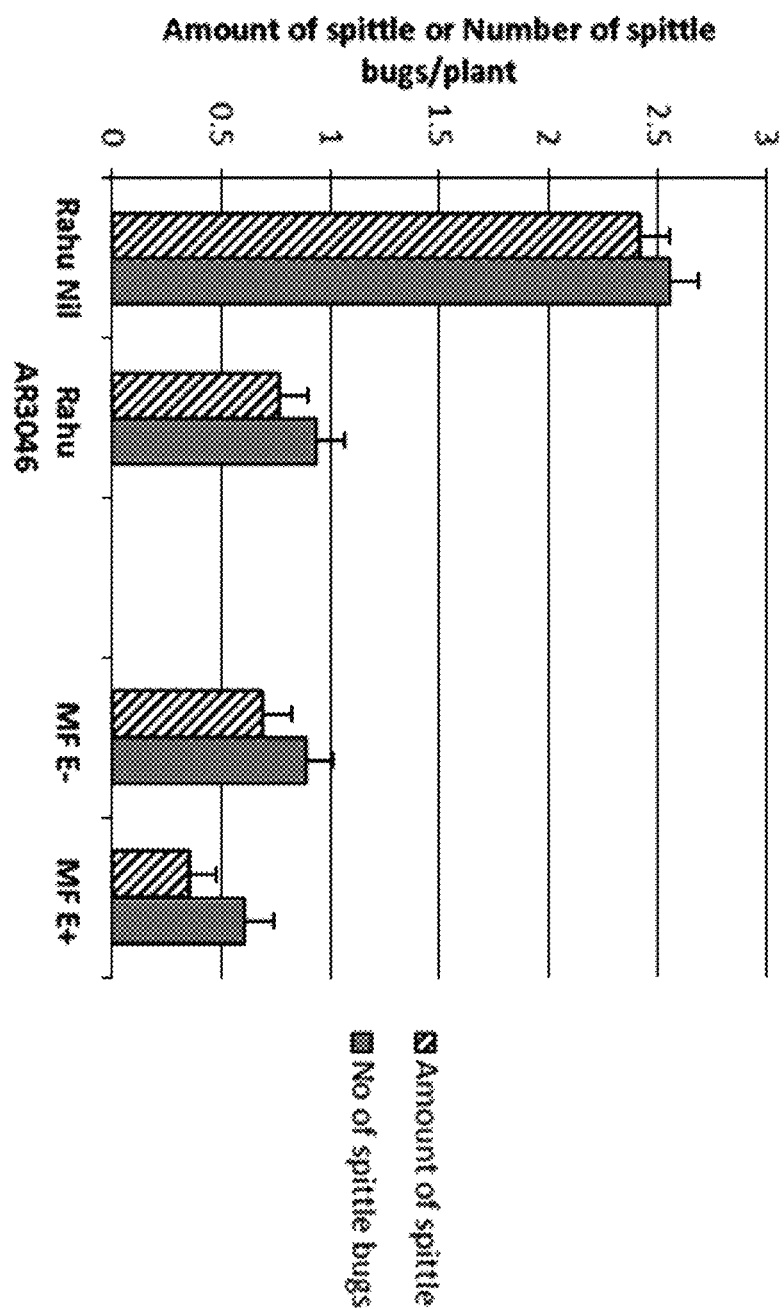
FIG. 3 shows the amount of spittle or Number of spittle bugs/plant observed on *Secale cereale* cultivar Rahu plants infected with AR3046 endophyte (Rahu AR3046), and on uninfected plants (Rahu Nil). Also shown is the amount of spittle or number of spittle bugs/plant observed on meadow fescue (*Festuca pratensis* syn. *Lolium pratense* syn. *Schedonorus pratensis*) plants infected with its naturally occurring endophyte, *Neotyphodium uncinatum* (MF E+) and on uninfected plants (MF E−).

*Secale* infected with AR3046 reduced both the number and amount of spit produced by spittle bug in comparison with endophyte-free (FIG. 3).

In the first experiment, significantly fewer spittle bugs were present on the AR3046 plants compared with endophyte-free throughout the experiment, while in the second experiment the reduction in numbers was significant only at the beginning of the experiment. In contrast to these results, endophyte-infected meadow fescue had no effect on numbers or feeding by spittle bug.

The results in this trial strongly suggest that the loline alkaloids produced by AR3046 are responsible for conferring at least some level of pest protection on infected *Secale* by reducing infestations of Spittle bugs on endophyte infected *Secale* plants. This is consistent with lolines being shown to have deterrent and pesticidal effects with other insects and plant pests (Schardl et. al., 2007; Bacetty et al., 2009a 2009b).

Example 13

Plant Disease Trials

Figure 4:
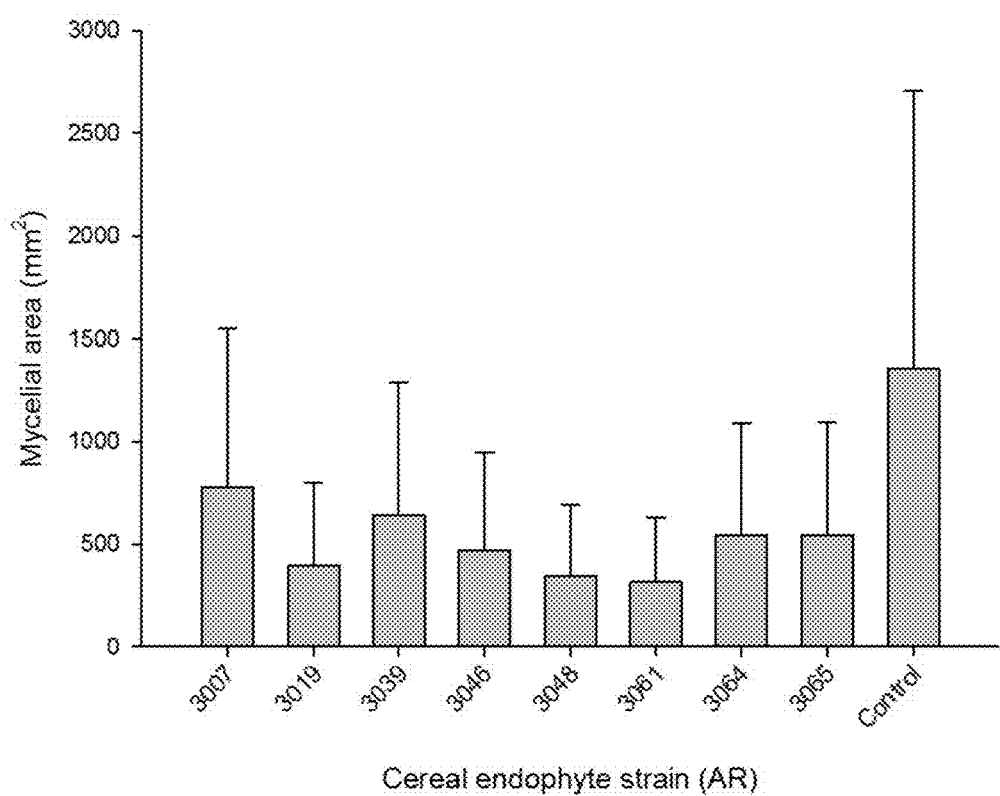
FIG. 4 shows that certain endophyte strains that significantly ($P \leq 0.05$) inhibited the mycelial growth of *Fusarium graminearum* in dual culture (data from unpublished research by Stuart Card, AgResearch Ltd).
Figure 5:
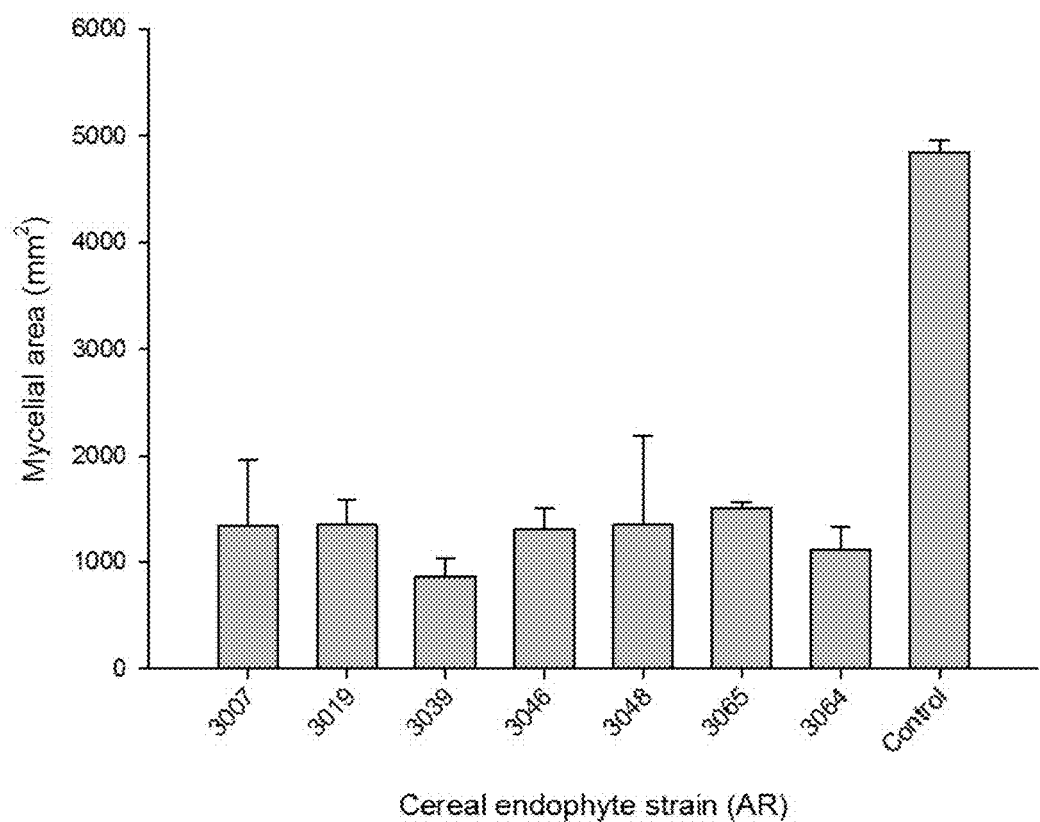
FIG. 5 shows cereal endophyte strains that significantly (P0.05) inhibited the mycelial growth of *Rhizoctonia solani* in dual culture (data from unpublished research by Stuart Card, AgResearch Ltd).

The following in vitro results to show the impact of selected endophytes on cereal fungal pathogens, including inhibition of the development of a range of pathogenic and saprotrophic fungi. For example a number of endophyte strains have significantly ($P \le 0.05$) inhibited the mycelial growth of *Fusarium graminearum* and *Rhizoctonia solani* (FIG. 4 and FIG. 5). These two pathogens are the causal agents of Fusarium head blight and bare patch, respectively, both devastating diseases of cereal crops. These endophytes have the potential to provide protection against many cereal diseases. Without wishing to be bound by theory, the inventors believe that although no mechanism/s of action has been identified to date to account for this inhibition, antibiosis through the production of unknown secondary metabolites is a likely mechanism.

The trial results demonstrated that a number of endophyte strains significantly (($P \le 0.05$) inhibited the mycelial growth of *Fusarium graminearum* (FIG. 4) and *Rhizoctonia solani* (FIG. 5).

Although the invention has been described by way of example and with reference to particular embodiments, it is to be understood that modifications and/or improvements may be made without departing from the scope of the invention.

In addition, where features or aspects of the invention are described in terms of Markush groups, those skilled in the art will recognise that the invention is also thereby described in terms of any individual member or subgroup of members of the Markush group.

The skilled person will appreciate that the invention as set forth and described herein is not limited solely to the aspects, embodiments, and examples as described, but also encompasses within the spirit and scope of the invention, those variations and modifications of the invention as would be obvious to the person of skill in the art (including the person of ordinary skill in the art) in view of the disclosures provided herein and the common general knowledge.

INDUSTRIAL APPLICATION

The epichloae endophyte strains, plant/fungal symbioses, seeds produced from such symbioses and methods of making such symbioses according to the invention as disclosed herein all have industrial application for the production of plants that are used for human or animal consumption

REFERENCES

Bacetty A, Snook M E, Glenn A E, Noe J P, Hill N, Culbreath A, Timper P, Bacon C W (2009a) Toxicity of endophyte-infected tall fescue alkaloids and grass metabolites on *Pratylenchus scribneri*. Phytopathology 99: 1336-1345

Bacetty A, Snook M E, Glenn A E, Noe J P, Nagabhyru P, Bacon C W (2009b) Chemotaxis disruption in *Pratylenchus Scribneri* by tall fescue root extracts and alkaloids. Journal of Chemical Ecology 35: 844-850

Blankenship J D, Spiering M J, Wilkinson H, Fannin F, Bush L P, Schardl C L (2001). Production of loline alkaloids by the grass endophyte, *Neotyphodium uncinatum*, in defined media. Phytochemistry 58: 395-401

Brownstein M J, Carpten J D, Smith J R (1996) Modulation of non-templated nucleotide addition by Taq DNA polymerase: Primer modifications that facilitate genotyping. BioTechniques 20: 1004-1010

Bush L P, Wilkinson H, Schardl C L (1997) Bioprotective Alkaloids of Grass-Fungal Endophyte Symbioses. Plant Physiology 114: 1-7

Casida J E, Quistad G B (1998) Golden Age of Insecticide Research: Past, Present, or Future? Annual Review of Entomology 43: 1-16.

Christensen M J (1995) Variation in the ability of Acremonium endophytes of *Lolium perenne, Festuca arundinacea* and *F. pratensis* to form compatible associations in the 3 grasses. Mycological Research 99: 466-470

Christensen M J, Bennett R J, Schmid J (2002) Growth of *Epichloë/Neotyphodium* and p-endophytes in leaves of *Lolium* and *Festuca* grasses. Mycological Research 106: 93-106

Christensen M J, Bennett R J, Schmid J (2001) Vascular bundle colonisation by *Neotyphodium* endophytes in natural and novel associations with grasses. Mycological Research 105: 1239-1245

Christensen M J, Leuchtmann A, Rowan D, Tapper B A (1993) Taxonomy of Acremonium Endophytes of Tall Fescue (Festuca-Arundinacea), Meadow Fescue (F-Pratensis) and Perennial Rye-Grass (Lolium-Perenne). Mycological Research 97: 1083-1092

Christensen M J, Simpson W R, Al Samarrai T (2000) Infection of tall fescue and perennial ryegrass plants by combinations of different *Neotyphodium* endophytes. Mycological Research 104: 974-978

Christensen M J, Saulsbury K, Simpson W R (2012) Conspicuous epiphytic growth of an interspecific hybrid *Neotyphodium* sp. endophyte on distorted host inflorescences. Fungal Biology 116: 42-48

Felsenstein, J. (2005) PHYLIP (Phylogeny Inference Package) version 3.6. Distributed by the author. Department of Genome Sciences, University of Washington, Seattle Garthwaite I, Sprosen J, Briggs L, Collin R, Towers N (1994) Food quality on the farm: Immunological detection of mycotoxins in New Zealand pastoral agriculture. Food & Agricultural Immunology 6: 123-129

Glenn A E, Bacon C W, Price R, Hanlin R T (1996) Molecular phylogeny of Acremonium and its taxonomic implications. Mycologia 88: 369-383

Huson D, Richter D, Rausch C, Dezulian T, Franz M, Rupp R (2007) Dendroscope: An interactive viewer for large phylogenetic trees. BMC bioinformatics 8: 460

Kennedy C W, Bush L P (1983) Effect of environment and management factors on the accumulation of N-acetyl and N-formyl loline alkaloids in tall fescue. Crop Science 23: 547-552

Koulman A, Lane G A, Christensen M J, Fraser K, Tapper B A (2007) Peramine and other fungal alkaloids are exuded in the guttation fluid of endophyte-infected grasses. Phytochemistry 68: 355-360

Latch G C M, Christensen M J (1985) Artificial Infection of Grasses with Endophytes. Annals of Applied Biology 107: 17-24

Malinowski D P, Belesky D P (2000) Adaptations of endophyte-infected cool-season grasses to environmental stresses: Mechanisms of drought and mineral stress tolerance. Crop Science: 40: 923-940

Marshall D, Tunali B, Nelson L R (1999) Occurrence of fungal endophytes in species of wild triticum. Crop Science 39: 1507-1512

Miller J S, Funk V A, Wagner W L, Barrie F, Hoch P C, Herendeen P (2011) Outcomes of the 2011 botanical nomenclature section at the XVIII International Botanical Congress. PhytoKeys 5: 1-3

Moon C D, Tapper B A, Scott B (1999) Identification of *Epichloë* endophytes in planta by a microsatellite-based PCR fingerprinting assay with automated analysis. Applied and Environmental Microbiology 65: 1268-1279

Moon C D, Craven K D, Leuchtmann A, Clements S L, Schardl C L (2004). Prevalence of interspecific hybrids amongst asexual fungal endophytes of grasses. *Molecular Ecology* 13 (6): 1455-1467

Porter J K (1994). Chemical constituents of grass endophytes. In:

Bacon, C. W., White Jr., J. F (Eds), Biotechnology of Endophytic Fungi of Grasses. CRC, Boca Raton, Fla., pp. 103-123

Rasmussen S, Lane G A, Mace W, Parsons A J, Fraser K, Xue H (2012) The use of genomics and metabolomics methods to quantify fungal endosymbionts and alkaloids in grasses. Methods in Molecular Biology 860: 213-226

Rowan D (1993) Lolitrems, peramine and paxilline: mycotoxins of the ryegrass/endophyte interaction. *Agriculture, Ecosystems and Environment* 44:, 103-122

Rowan D, Latch G C M (1994) Utilization of endophyte-infected perennial ryegrasses for increased insect resistance. In: Bacon C W, White Jr. J F (eds), Biotechnology of Endophyte Fungi of Grasses. CRC Press, Boca Raton, Fla., pp. 169-183

Sanger F, Nicklen S, Coulson A R (1977), DNA sequencing with chain-terminating inhibitors, Proceedings of the National Academy of Sciences USA 74 (12): 5463-5467

Schardl C L, Craven K D, Speakman S, Stromberg A, Lindstrom A, Yoshida R (2008). A novel test for host-symbiont codivergence indicates ancient origin of fungal endophytes in grasses. Syst Biol. 57: 483-498

Schardl C L, Grossman R B, Nagabhyru P, Faulkner J R, Mallik U P (2007) Loline alkaloids: Currencies of mutualism. Phytochemistry 68: 980-996

Schardl C L, Young C A, Faulkner J R, Florea S, Pan J (2012) Chemotypic diversity of epichloae fungal symbionts of grasses. Fungal Ecology 5: 331-344

Schuelke M (2000) An economic method for the fluorescent labelling of PCR fragments. Nature Biotechnology 18: 233-234

Simpson W R, Mace W J (2012) Novel associations between epichloae endophytes and grasses: Possibilities and outcomes. In 'Epichloae, endophytes of cool season grasses: Implications, utilization and biology.' (Eds C A Young, G E Aiken, R L McCulley, J R Strickland, C L Schardl.) pp. 35-39. (The Samuel Roberts Noble Foundation: Ardmore, Okla.)

Simpson W R, Schmid J, Singh J, Faville M J, Johnson R D (2012) A morphological change in the fungal symbiont *Neotyphodium lolii* induces dwarfing in its host plant *Lolium perenne*. Fungal Biology 116: 234-240

Subramanian A R, Kaufmann M, Morgenstern B (2008) DIALIGN-TX: greedy and progressive approaches for segment-based multiple sequence alignment. Algorithms for Molecular Biology 3: article 6

Tanaka A, Tapper B A, Popay A, Parker E J, Scott B (2005) A symbiosis expressed non-ribosomal peptide synthetase from a mutualistic fungal endophyte of perennial ryegrass confers protection to the symbiotum from insect herbivory. Molecular Microbiology 57: 1036-1050

Tsai H F, Liu J S, Staben C, Christensen M J, Latch G C, Siegel M R, Schardl C L (1994). Evolutionary diversification of fungal endophytes of tall fescue grass by hybridization with *Epichloë* species. Proc. Natl. Acad. Sci. USA 91 (7): 2542-2546

Welty R E, Azevedo M D, Cooper T M (1987) Influence of moisture content, temperature, and length of storage on seed germination and survival of endophytic fungi in seeds of tall fescue and perennial ryegrass. Phytopathology 77: 893-900

Wilkinson H, Siegel M R, Blankenship J D, Mallory A C, Bush L P, Schardl C L (2000). Contribution of fungal loline alkaloids to protection from aphids in a grass-endophyte mutualism. Molecular Plant Microbe Interactions 13: 1027-1033

Yates S G, Fenster J C, Bartelt R J (1989) Assay of tall fescue seed extracts, fractions and alkaloids using the large milkweed bug. Journal of Agriculture and Food Chemistry 37: 354-357

Zejda J E, McDuffie H, Dosman J A (1993) Epidemiology of health and safety risks in agriculture and related industries—Practical applications for rural physicians. Western Journal of Medicine 158: 56-63

Zhang, D X, Nagabhyru P, Blankenship J D, Schardl C L (2010) Are loline alkaloid levels regulated in grass endophytes by gene expression or substrate availability? Plant Signaling and Behavior 5 (11): 1419-22

Description of the Microorganism Deposits Made Under the Budapest Treaty

The following biological deposits have been made under the terms of the Budapest Treaty on the International Recognition of the Deposit of Micro-organisms for the Purposes of Paten procedure

| Deposit Identification Reference | International Depository Designation | Date of Deposit |
| --- | --- | --- |
| AR 3039 | NRRL 50716 | 6 Mar. 2012 |
| AR 3046 | NRRL 50576 | 13 Oct. 2011 |
| AR 3049 | NRRL 50577 | 13 Oct. 2011 |
| AR 3050 | NRRL 50578 | 13 Oct. 2011 |
| AR 3064 | NRRL 50718 | 6 Mar. 2012 |
| AR 3067 | NRRL 50719 | 6 Mar. 2012 |
| AR 3068 | NRRL 50720 | 6 Mar. 2012 |
| AR 3073 | NRRL 50721 | 6 Mar. 2012 |
| AR 3074 | NRRL 50722 | 6 Mar. 2012 |
| AR 3076 | NRRL 50723 | 6 Mar. 2012 |
| AR 3078 | NRRL 50724 | 6 Mar. 2012 |

Certificates of Deposit and Statements of Viability for the above deposited micro-organisms are appended below.

What we claim is:

1. A *Secale* spp. plant infected with an epichloae fungal endophyte wherein *Secale* spp. is not a natural host of the endophyte, wherein the epichloae fungal endophyte is selected from the group consisting of AR3039 (NRRL# 50716), AR3046 (NRRL# 50576), AR3049 (NRRL#50577), AR3050 (NRRL# 50578), AR3064 (NRRL# 50718), AR3067(NRRL# 50719), AR3068 (NRRL# 50720), AR3073 (NRRL# 50721), AR3074(NRRL# 50722), AR3076 (NRRL# 50723), and AR3078 (NRRL# 50724), or combinations thereof, and wherein the plant and endophyte form a stable symbiotic association that allows the plant to progress through a normal life cycle.

2. The *Secale* spp. plant according to claim 1, wherein the epichloae fungal endophyte is selected from the group consisting of AR3039 (NRRL# 50716), AR3046 (NRRL# 50576), AR3050 (NRRL# 50578), AR3067 (NRRL# 50719), AR3068(NRRL# 50720), AR3074 (NRRL# 50722), and AR3078 (NRRL# 50724).

3. The *Secale* spp. plant according to claim 1, wherein the epichloae fungal endophyte is selected from the group consisting of AR3046 (NRRL# 50576), AR3050 (NRRL# 50578), and AR3068 (NRRL# 50720).

4. The *Secale* spp. plant according to claim 1, wherein the *Secale* spp. plant infected with the fungal endophyte shows a normal morphological phenotype.

5. The *Secale* spp. plant according to claim 1, wherein the *Secale* spp. plant infected with the fungal endophyte produces loline alkaloids and/or peramine.

6. The *Secale* spp. plant according to claim 1, wherein the *Secale* spp. plant infected with the fungal endophyte has increased resistance to one or more pests or increased resistance to at least one plant disease, wherein the pests are selected from the group consisting of (1) species of aphids (Aphididae); (2) species of grass and cereal flies (Agromyzidae; Anthomyiidae, Chloropidae, Cephidae and Cecidomyiidae); (3) species of thrips (Thripidae); (4) species of grasshoppers and crickets (Acrididae and Gryllidae); (5) species of bugs (Lygaeidae); (6) species of weevils (Curculionidae); (7) species of armyworm and cutworm (Noctuidae); (8) species of leaf beetles (Chysomelidae); (9) species of white grubs (Scarabaeidae); (10) species of mealybug (Pseudococcidae and Coccidae); (11) species of wireworms (Elateridae); species of beetles (Carabidae); (13) species of mites (Eriophyidae and Penthaleidae); (14) species of stored product pests (Curculionidae, Silvanidae, Pyralidae, Gelechiidae, Tenebrionidae, Bostrichidae); (15) species of froghopper (Cercopoidea); (16) species of nematodes; (17) and species of slugs, and wherein the at least one plant disease is caused by a plant pathogen selected from the group consisting of Barley yellow dwarf virus (Leteovirus), wheat soil-borne mosaic virus (Furovirus) and wheat streak mosaic virus (Tritimovirus), *Xanthomonas campestris*, *Pseudomonas syringae*, *Colletotrichum graminicola*, *Glomerella graminicola* [teleomorph], *Alternaria* spp., *Cladosporium herbarum*, *Mycosphaerella tassiana* [teleomorph], *Epicoccum* spp., *Sporobolomyces* spp., *Stemphylium* spp., *Bipolaris sorokiniana*, *Cochliobolus sativus* [teleomorph], *Fusarium* spp., *Tilletia caries*, *Tilletia tritici*, *Tilletia laevis*, *Tilletia foetida*, *Hymenula cerealis*, *Cephalosporium gramineum*, *Helminthosporium sativum*, *Cochliobolus sativus* [teleomorph], *Coprinus sychromorbidus*, *Dilophospora alopecuri*, *Tilletia controversa*, *Claviceps purpurea*, *Sphacelia segetum* [anamorph], *Fusarium culmorum*, *Pseudoseptoria donacis*, *Selenophoma donacis*, *Neovossia indica*, *Tilletia indica*, *Puccinia recondita*, *Aecidium clematidis* [anamorph], *Cercosporidium graminis*, *Scolicotrichum graminis*, *Phaeosphaeria herpotrichoides*, *Leptosphaeria herpotrichoides*, *Ustilago tritici*, *Microdochium nivale*, *Fusarium nivale*, *Monographella nivalis* [teleomorph], *Erysiphe graminis*, *Pythium aphanidermatum*, *Pythium arrhenomanes*, *Pythium debaryanum*, *Pythium graminicola*, *Pythium ultimum*, *Gibberella zeae*, *Fusarium graminearum* [anamorph], *Septoria secalis*, *Septoria tritici*, *Mycosphaerella graminicola* [teleomorph], *Rhizoctonia cerealis*, *Rhizoctonia solani*, *Rhizoctonia zeae*, *Blumeria* spp., *Ceratobasidium cereale* [teleomorph], *Myriosclerotinia borealis*, *Sclerotinia borealis*, *Typhula idahoensis*, *Typhula incarnate*, *Typhula ishikariensis*, *Typhula ishikariensis* var. *canadensis*, *Stagonospora nodorum*, *Septoria nodorum*, *Phaeosphaeria nodorum* [teleomorph], *Leptosphaeria nodorum*, *Urocystis occulta*, *Puccinia graminis*, *Aspergillus* spp., *Nigrospora* spp., *Penicillium* spp., *Rhizopus* spp., *Pseudocercosporella herpotrichoides*, *Tapesia acuformis* [teleomorph], *Uredo glumarum* [anamorph], *Pyrenophora tritici-repentis*, Drechslera tritici-*repentis* [anamorph], *Helminthosporium tritici-repentis*, *Puccinia triticina*, *Pythium* spp., *Rhynchosporium secalis*, *Puccinia striiformis*, *Gaeumannomyces graminis* and *Fusarium pseudo graminearum*.

7. The *Secale* spp. plant according to claim 1, wherein the plant pathogen is *Puccinia recondita*, *Puccinia triticina*, *Puccinia graminis*, *Fusarium* spp., *Pythium* spp., *Rhynchosporium secalis*, *Puccinia striiformis*, *Gaeumannomyces graminis*, *Rhizoctonia solani* or *Fusarium pseudograminearum*.

8. The *Secale* spp. plant according to claim 1 wherein the *Secale* spp. is selected from the group consisting of *Secale cereale*, *Secale montanum*, *Secale strictum*, *Secale sylvestre* and *Secale vavilovii*.

9. The *Secale* spp. plant according to claim 1 wherein the *Secale* spp. is *Secale cereale*.

10. A method of making a stable host plant/epichloae fungal endophyte combination comprising artificially infecting a *Secale* spp. plant with at least one epichloae fungal endophyte that forms a stable combination with the inoculated plant, wherein the epichloae fungal endophyte is selected from the group consisting of AR3039 (NRRL# 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073 (NRRL# 50721), AR3074(NRRL# 50722), AR3076 (NRRL# 50723), and AR3078 (NRRL# 50724), and combinations thereof, and wherein the host plant shows no external symptoms of endophyte infection.

11. The method according to claim 10, wherein the *Secale* spp. plant is selected from the group consisting of *Secale cereale*, *Secale montanum*, *Secale strictum*, *Secale sylvestre* and *Secale vavilovii*.

12. A method of conferring at least some level of pest protection on a host *Secale* spp. plant comprising artificially infecting a *Secale* spp. plant with at least one epichloae fungal endophyte, wherein the epichloae fungal endophyte is selected from the group consisting of AR3039 (NRRL# 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073 (NRRL# 50721), AR3074 (NRRL# 50722), AR3076 (NRRL# 50723), and AR3078 (NRRL# 50724), and combinations thereof, and wherein the fungal endophyte-*Secale* plant combination produces at least one alkaloid at a level sufficient to confer at least some level of pest protection on the host plant.

13. The method according to claim 12, wherein the at least one alkaloid is an alkaloid selected from the group consisting of peramine, N-acetylnorloline, loline, N-formylloline, N-acetylloline, and N-methylloline.

14. The method according to claim 12, wherein the *Secale* spp. host plant is selected from the group consisting of *Secale cereale*, *Secale montanum*, *Secale strictum*, *Secale sylvestre* and *Secale vavilovii*.

15. A *Secale* spp. seed infected with at least one epichloae fungal endophyte, wherein the epichloae fungal endophyte is selected from the group consisting of AR3039 (NRRL# 50716), AR3046 (NRRL# 50576), AR3049 (NRRL#50577), AR3050 (NRRL# 50578), AR3064 (NRRL# 50718), AR3067 (NRRL# 50719), AR3068 (NRRL# 50720), AR3073(NRRL# 50721), AR3074 (NRRL# 50722), AR3076 (NRRL# 50723), and AR3078 (NRRL# 50724), and combinations thereof.

16. The *Secale* spp. seed according to claim 15, wherein the seed is a seed of a *Secale* spp. selected from the group consisting of *Secale cereale*, *Secale montanum*, *Secale strictum*, *Secale sylvestre* and *Secale vavilovii*.

17. The *Secale* spp. seed according to claim 15, wherein the epichloae fungal endophyte is selected from the group consisting of AR3039 (NRRL# 50716), AR3046 (NRRL# 50576), AR3050 (NRRL# 50578), AR3067 (NRRL# 50719), AR3068(NRRL# 50720), AR3074 (NRRL# 50722), and AR3078 (NRRL# 50724).

18. The *Secale* spp. seed according to claim 15, wherein the epichloae fungal endophyte is selected from the group consisting of AR3046 (NRRL# 50576), AR3050 (NRRL# 50578), and AR3068 (NRRL# 50720).

* * * * *

SEQUENCE LISTING

<160> NUMBER OF SEQ ID NOS: 30

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
tgtaaaacga cggccagt                                                   18

<210> SEQ ID NO 2
<211> LENGTH: 7
<212> TYPE: DNA
<213> ORGANISM: Artificial Sequence
<220> FEATURE:
<223> OTHER INFORMATION: Primer

<400> SEQUENCE: 2 gtttctt                                                                7

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
cgctcagggc tacatacacc atgg                                            24

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ctcatcgagt aacgcaggcg acg                                             23

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
tacctctgca cggtgtattc c                                               21

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
tgcataacac tcaccttata gtcg                                            24

<210> SEQ ID NO 7
<211> LENGTH: 22
<212> TYPE: DNA
<213> ORGANISM: Artificial Sequence

```
<220> FEATURE:
<223> OTHER INFORMATION: Primer

<400> SEQUENCE: 7
gcgttgagga ggctagatag aa                                                  22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ttccaagctg aacaaaagtc aa                                                  22

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
gatgacgtat cttgatgcta ccac                                                24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
cgtgtataaa gttcgggatc ctat                                                24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
gagatatccc gtctcctgat ctaa                                                24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cacagcgtta cactatcaac ttcc                                                24

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
cacagcgtta cactatcaac ttcc                                                24
```

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
agacaggtaa gaagttttcc cctt                                              24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
agctttccaa tgacgacata cata                                              24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
taatttaggg tagcattttc tccg                                              24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ggtccctatt ctaatgcagg tatg                                              24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
cagtgtacgg gactttgtca atac                                              24

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
tgtataataa acatggcgtg ctct                                              24

<210> SEQ ID NO 20
<211> LENGTH: 24
<212> TYPE: DNA
<213> ORGANISM: Artificial Sequence
<220> FEATURE:
<223> OTHER INFORMATION: Primer

```
<400> SEQUENCE: 20
gtgttgaaag ttgttggatc actc                                    24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
cgaaattgta gactatgttg gagc                                    24

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
gtagatgtat tttgagcagg gctt                                    24

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
gagtgagacc cggtgtagta agtc                                    24

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gagtcattct tcgtccattg tctt                                    24

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
gaaatgaggc gtctatctta aagc                                    24

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
tttcttgatt tccaaagaac aaca                                    24

<210> SEQ ID NO 27
```

```
<211> LENGTH: 24
<212> TYPE: DNA
<213> ORGANISM: Artificial Sequence
<220> FEATURE:
<223> OTHER INFORMATION: Primer

<400> SEQUENCE: 27
ctgctagaca tacttggaac atgg                                          24

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
cagtcgaata atttagggag catt                                          24

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tcggcctcac gacgcacaac                                               20

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
cccatacatt acacctttct ggcg                                          24
```